United States Patent
Simaan et al.

(10) Patent No.: US 11,596,770 B2
(45) Date of Patent: Mar. 7, 2023

(54) MULTI-ARTICULATED CATHETERS WITH SAFETY METHODS AND SYSTEMS FOR IMAGE-GUIDED COLLABORATIVE INTRAVASCULAR DEPLOYMENT

(71) Applicant: Vanderbilt University, Nashville, TN (US)

(72) Inventors: Nabil Simaan, Nashville, TN (US); Giuseppe Del Giudice, Nashville, TN (US); Colette Abah, Nashville, TN (US); Rohan V. Chitale, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 17/760,695

(22) PCT Filed: Sep. 16, 2020

(86) PCT No.: PCT/US2020/051009
§ 371 (c)(1),
(2) Date: Mar. 15, 2022

(87) PCT Pub. No.: WO2021/055428
PCT Pub. Date: Mar. 25, 2021

(65) Prior Publication Data
US 2022/0355075 A1 Nov. 10, 2022

Related U.S. Application Data

(60) Provisional application No. 62/901,114, filed on Sep. 16, 2019.

(51) Int. Cl.
*A61B 34/30* (2016.01)
*A61B 34/00* (2016.01)
(Continued)

(52) U.S. Cl.
CPC ......... *A61M 25/0113* (2013.01); *A61B 17/22* (2013.01); *A61B 34/20* (2016.02);
(Continued)

(58) Field of Classification Search
CPC ................................................. A61B 2034/303
See application file for complete search history.

(56) References Cited

U.S. PATENT DOCUMENTS

| | | |
|---|---|---|
| 4,930,494 A | 6/1990 | Takehana et al. |
| 8,116,886 B2 | 2/2012 | Simaan et al. |

(Continued)

FOREIGN PATENT DOCUMENTS

| | | |
|---|---|---|
| WO | 2003099152 | 12/2003 |
| WO | 2018204202 | 11/2018 |
| WO | 2019074786 | 4/2019 |

OTHER PUBLICATIONS

Abah et al., "Towards Semi-Automated Mechanical Thrombectomy: Path Planning Considerations for a Double Articulated Microcatheter," in Hamlyn Symposium on Surgical Robotics, 2019, pp. 1-2.

(Continued)

*Primary Examiner* — Martin T Ton
(74) *Attorney, Agent, or Firm* — Michael Best & Friedrich LLP

(57) ABSTRACT

Systems and method for controlling the bending of a robotic catheter. A control backbone of the robotic catheter is coupled to a linear movement stage by a spring and linear movement of the control backbone causes a controllable bending of the robotic catheter. A sensor monitors a deflection of the spring and the bending of the catheter is controlled based on the spring deflection signal from the sensor. The spring allows passive bending of the robotic catheter without movement of the active linear movement stage and, conversely, allows external forces applied to the robotic (Continued)

catheter to limit a bending movement of the robotic catheter caused by—movement of the active linear movement stage. In some implementations, the robotic catheter includes a selectively deployable tip mechanism for deploying a steerable tip or for selectively exposing side windows on the catheter for increasing traction for clot removal.

18 Claims, 12 Drawing Sheets

(51) Int. Cl.
    A61B 34/20    (2016.01)
    A61M 25/01    (2006.01)
    A61B 17/22    (2006.01)

(52) U.S. Cl.
    CPC .............. A61B 34/30 (2016.02); A61B 34/74 (2016.02); A61M 25/0133 (2013.01); A61B 2017/22079 (2013.01); A61B 2034/301 (2016.02); A61B 2034/303 (2016.02); A61M 2025/0166 (2013.01); A61M 2205/3327 (2013.01); A61M 2205/502 (2013.01)

(56) References Cited

U.S. PATENT DOCUMENTS

| | | | |
|---|---|---|---|
| 9,539,726 B2 | 1/2017 | Simaan et al. | |
| 10,300,599 B2 | 5/2019 | Simaan et al. | |
| 2010/0204646 A1* | 8/2010 | Plicchi | A61B 34/30 604/95.01 |
| 2012/0123441 A1* | 5/2012 | Au | A61B 34/30 606/130 |
| 2019/0247050 A1 | 8/2019 | Goldsmith | |
| 2020/0253669 A1* | 8/2020 | Diolaiti | A61B 34/76 |
| 2020/0383670 A1* | 12/2020 | Okumura | A61B 1/0052 |

OTHER PUBLICATIONS

Adeoye et al., "Geographic access to acute stroke care in the United States," Stroke, vol. 45, No. 10, pp. 3019-3024, 2014.
Akter et al., "3D CT to 2D low dose single-plane fluoroscopy registration algorithm for in-vivo knee motion analysis," 2014 36th Annual International Conference of the IEEE Engineering in Medicine and Biology Society, EMBC 2014, pp. 5121-5124, 2014.
Akter et al., "Improved robustness of 3D CT to 2D fluoroscopy image registration using log polar transforms," ICECTE 2016—2nd International Conference on Electrical, Computer and Telecommunication Engineering, 2017, pp. 8-10.
Ali et al., "Steerable Catheters in Cardiology: Classifying Steerability and Assessing Future Challenges," IEEE Transactions on Biomedical Engineering, vol. 63, No. 4. IEEE, pp. 679-693, 2016.
Allard et al., "Multimodality vascular imaging phantoms: A new material for the fabrication of realistic 3D vessel geometries," Medical Physics, vol. 36, No. 8, pp. 3758-3763, 2009.
Antoniou et al., "Clinical applications of robotic technology in vascular and endovascular surgery.," Journal of vascular surgery, vol. 53, No. 2, pp. 493-499, Feb. 2011.
Ayvali et al., "Towards a discretely actuated steerable cannula," Proceedings—IEEE International Conference on Robotics and Automation, pp. 1614-1619, 2012.
Baek et al., "Number of Stent Retriever Passes Associated With Futile Recanalization in Acute Stroke," pp. 2088-2095, 2018.
Baert et al., "Three-Dimensional Guide-Wire Reconstruction from Biplane Image Sequences for Integrated Display in 3-D Vasculature," IEEE Transactions on Medical Imaging, vol. 22, No. 10, pp. 1252-1258, 2003.
Bai et al., "Worldwide experience with the robotic navigation system in catheter ablation of atrial fibrillation: Methodology, efficacy and safety," Journal of Cardiovascular Electrophysiology, vol. 23, No. 8, pp. 820-826, 2012.
Bajo et al., "A Telerobotic System for Trans-nasal Micro-Surgery of the Throat," in IEEE International Conference on Robotics and Automation, 2013, pp. 232-238.
Bajo et al., "Compliant motion control for multisegment continuum robots with actuation force sensing," IEEE Transactions on Robotics, vol. 30, No. 4, pp. 890-902, 2014.
Bajo et al., "Configuration and joint feedback for enhanced performance of multi-segment continuum robots," in Proceedings—IEEE International Conference on Robotics and Automation, 2011, pp. 2905-2912.
Bajo et al., "Constrained motion control of multisegment continuum robots for transurethral bladder resection and surveillance," Proceedings—IEEE International Conference on Robotics and Automation, pp. 5837-5842, 2013.
Bajo et al., "Finding lost wrenches: Using continuum robots for contact detection and estimation of contact location," in 2010 IEEE International Conference on Robotics and Automation, 2010, pp. 3666-3673.
Bajo et al., "Integration and preliminary evaluation of an Insertable Robotic Effectors Platform for Single Port Access Surgery," Proceedings—IEEE International Conference on Robotics and Automation, pp. 3381-3387, 2012.
Bajo et al., "Kinematics-based detection and localization of contacts along multisegment continuum robots," IEEE Transactions on Robotics, vol. 28, No. 2, pp. 291-302, 2012.
Bajo et al., "Trans-Nasal Robotic Micro-Surgery of the Throat: A Cadaveric Feasibility Study," in The 6th Hamlyn Symposium on Surgical Robotics, 2013, pp. 27-28.
Bajo et al., "Robotic-assisted micro-surgery of the throat: The trans-nasal approach," in 2013 IEEE International Conference on Robotics and Automation, 2013, pp. 232-238.
Bajo, "Control, Sensing, and Telemanipulation of Surgical Continuum Robots," Vanderbilt University, 2013.
Balami et al., "Complications of endovascular treatment for acute ischemic stroke: Prevention and management," International Journal of Stroke, vol. 13, No. 4, pp. 348-361, 2018.
Benjamin et al., Heart Disease and Stroke Statistics 2017 Update: A Report from the American Heart Association, vol. 135, No. 10. 2017.
Berkhemer et al., "A Randomized Trial of Intraarterial Treatment for Acute Ischemic Stroke," New England Journal of Medicine, vol. 372, No. 1, pp. 11-20, 2015.
Beyar et al., "Remote-control percutaneous coronary interventions: Concept, validation, and first-in-humans pilot clinical trial," Journal of the American College of Cardiology, vol. 47, No. 2, pp. 296-300, 2006.
Bhattacharyya et al., "Characterization of Constraints in Flexible Unknown Environments," in IEEE International Conference on Robotics and Automation, 2013, p. accepted.
Bhattacharyya, "Motion Planning and Constraint Exploration for Robotic Surgery," M.Sc. thesis,(Advisor: N. Simaan), Mechanical Engineering, Vanderbilt University, 2011.
Biffl et al., "Blunt carotid arterial injuries: Implications of a new grading scale," Journal of Trauma—Injury, Infection and Critical Care, vol. 47, No. 5, pp. 845-853, 1999.
Bonatti et al., "Robotic technology in cardiovascular medicine," Nature Reviews Cardiology, vol. 11, No. 5, pp. 266-275, 2014.
Bracard et al., "Mechanical thrombectomy after intravenous alteplase versus alteplase alone after stroke (THRACE): a randomised controlled trial," The Lancet Neurology, vol. 15, No. 11, pp. 1138-1147, 2016.
Brand et al., "A constrained theory of a Cosserat point for the numerical solution of dynamic problems of non-linear elastic rods with rigid cross-sections," International Journal of Non-Linear Mechanics, vol. 42, No. 2, pp. 216-232, 2007.
Cabras, "3D Pose Estimation for the Control of Flexible Instruments in Robotic Endoscopic Surgery", Thesis, Universite de Strasbourg, 200 pages, 2016.
C. D. C. & Prevention, "Stroke Facts." [Online]. Available: https://www.cdc.gov/stroke/facts.htm.

(56) References Cited

OTHER PUBLICATIONS

Campbell et al., "Endovascular Therapy for Ischemic Stroke with Perfusion-Imaging Selection," New England Journal of Medicine, vol. 372, No. 11, pp. 1009-1018, 2015.
Canero et al., "3D curve reconstruction by biplane snakes," IEEE, 2000, pp. 563-566.
Cao et al., "A new production method of elastic silicone carotid phantom based on MRI acquisition using rapid prototyping technique," Proceedings of the Annual International Conference of the IEEE Engineering in Medicine and Biology Society, EMBS, pp. 5331-5334, 2013.
Carlone et al., "From angular manifolds to the integer lattice: Guaranteed orientation estimation with application to pose graph optimization," IEEE Transactions on Robotics, vol. 30, No. 2, pp. 475-492, 2014.
Cercenelli et al., "CathROB: A Highly Compact and Versatile Remote Catheter Navigation System," Applied Bionics and Biomechanics, vol. 2017, pp. 1-13, 2017.
Chitalia et al., "Design, Modeling and Control of a 2-DoF Robotic Guidewire", IEEE ICRA, 2018, pp. 32-37.
Choi et al., "Regional Availability of Mechanical Embolectomy for Acute Ischemic Stroke in California, 2009 to 2010," Stroke, vol. 46, No. 3, pp. 762-768, 2015.
Da Costa et al., "Remote-controlled magnetic pulmonary vein isolation using a new three-dimensional non-fluoroscopic navigation system: A single-centre prospective study," Archives of Cardiovascular Diseases, vol. 106, No. 8-9, pp. 423-432, 2013.
Dall et al., "Supply and demand analysis of the current and future US neurology workforce," Neurology, vol. 81, No. 5, pp. 470-478, 2013.
Del Giudice et al., "Comparison of Two Endovascular Steerable Robotic Catheters for Percutaneous Robot-Assisted Fibroid Embolization," Cardiovascular and Interventional Radiology, vol. 41, No. 3, pp. 483-488, 2018.
Del Giudice et al., "Design Considerations for Continuum Robot Actuation Units Enabling Dexterous Transurethral Bladder Cancer Resection,", ASME Mechanisms and Robotics Conference, 2016, pp. 1-10.
Dharamsi et al., "Evaluation of a Telerobotic System for Transnasal Surgery of the Larynx and Airways in Cadavers.," Otolaryngology—head and neck surgery : official journal of American Academy of Otolaryngology—Head and Neck Surgery, vol. 151, No. 1, pp. 107-111, 2014.
Dibildox et al., "3D / 3D registration of coronary CTA and biplane XA reconstructions," vol. 41, No. 9, pp. 1-10, 2014.
Ding et al., "Design and Coordination Kinematics of an Insertable Robotic Effectors Platform for Single-Port Access Surgery," IEEE/ASME Transactions on Mechatronics, pp. 1-13, 2012.
Ding et al., "Design, simulation and evaluation of kinematic alternatives for insertable robotic effectors platforms in single port access surgery," Proceedings—IEEE International Conference on Robotics and Automation, pp. 1053-1058, 2010.
Dumont et al., "Aspiration thrombectomy in concert with stent thrombectomy," Journal of NeuroInterventional Surgery, vol. 6, No. 4, pp. e26-e26, 2014.
Dupont et al., "Torsional kinematic model for concentric tube robots," in IEEE International Conference on Robotics and Automation, 2009, pp. 3851-3858.
Faddis et al., "Magnetic Guidance System for Cardiac Electrophysiology: A Prospective Trial of Safety and Efficacy in Humans," Journal of the American College of Cardiology, vol. 42, No. 11, pp. 1952-1958, 2003.
Faddis et al., "Novel, magnetically guided catheter for endocardial mapping and radiofrequency catheter ablation," Circulation, vol. 106, No. 23, pp. 2980-2985, 2002.
Fagogenis et al., "Autonomous robotic intracardiac catheter navigation using haptic vision," Science Robotics, vol. 4, No. 29, 2019.
Faion et al., "Recursive Bayesian calibration of depth sensors with non-overlapping views.," Fusion, pp. 757-762, 2012.
Fan et al., "Decentralized and recursive identification for cooperative manipulation of unknown rigid body with local measurements," 2017 IEEE 56th Annual Conference on Decision and Control, CDC 2017, vol. 2018—Janua, No. Cdc, pp. 2842-2849, 2018.
Fayad et al., "Noninvasive in vivo human coronary artery lumen and wall imaging using black-blood magnetic resonance imaging.," Circulation, vol. 102, No. 5, pp. 506-510, 2000.
Froehler et al., "Interhospital Transfer Before Thrombectomy Is Associated With Delayed Treatment and Worse Outcome in the STRATIS Registry (Systematic Evaluation of Patients Treated With Neurothrombectomy Devices for Acute Ischemic Stroke)," Circulation, vol. 136, No. 24, pp. 2311-2321, 2017.
Fu et al., "Development of a novel robotic catheter system for endovascular minimally invasive surgery," in 2011 IEEE/ICME International Conference on Complex Medical Engineering, CME 2011, 2011, pp. 400-405.
Fu et al., "Steerable catheters in minimally invasive vascular surgery," The international journal of medical robotics + computer assisted surgery : MRCAS, vol. 5, pp. 381-391, 2009.
Fukuda et al., "Micro active catheter system with multi degrees of freedom," pp. 2290-2295, 2002.
Garbin et al., "Dual-Continuum Design Approach for Intuitive and Low-Cost Upper Gastrointestinal Endoscopy", IEEE Trans Biomed Eng., 2018, pp.
Ghoshhajra et al., "Real-time fusion of coronary CT angiography with x-ray fluoroscopy during chronic total occlusion PCI," European Radiology, vol. 27, No. 6, pp. 2464-2473, 2017.
Gilitschenski et al., "A New Probability Distribution for Simultaneous Representation of Uncertain Position and Orientation," Proceedings of the 17th International Conference on Information Fusion (Fusion 2014), pp. 1-7, 2014.
Gilitschenski et al., "Unscented Orientation Estimation Based on the Bingham Distribution," IEEE Transactions on Automatic Control, vol. 61, No. 1, pp. 172-177, 2016.
Glover et al., "Monte Carlo Pose Estimation with Quaternion Kernels and the Bingham Distribution," Robotics: Science and Systems VII, 2011.
Goldman et al., "Compliant Motion Control for Multisegment Continuum Robots with Actuation Force Sensing", IEEE Transactions on Robotics, 2014, vol. 30, No. 4, pp. 890-902.
Goldman et al., "Algorithms for autonomous exploration and estimation in compliant environments," Robotica, vol. 31, No. 1, pp. 1-17, 2012.
Goldman et al., "Compliant motion control for continuum robots with intrinsic actuation sensing," Proceedings—IEEE International Conference on Robotics and Automation, pp. 1126-1132, 2011.
Goldman et al., "Design and Performance Evaluation of a Minimally Invasive Telerobotic Platform for Transurethral Surveillance and Intervention," IEEE Transactions on Biomedical Engineering, pp. 1-1, 2013.
Goldman, "Analysis, Algorithms, and Control for Intelligent Surgical Exploration and Intervention," Ph.D. Dissertation, Mechanical Engineering, Columbia University, 2011, 149 pages.
Goyal et al., "Endovascular thrombectomy after large-vessel ischaemic stroke: a meta-analysis of individual patient data from five randomised trials", Lancet, 2016, vol. 387, No. 10029, pp. 1723-1731.
Goyal et al., "Randomized Assessment of Rapid Endovascular Treatment of Ischemic Stroke," New England Journal of Medicine, vol. 372, No. 11, pp. 1019-1030, Mar. 2015.
Grimson, "2D-3D Rigid Body Registration of X-ray Fluoroscopic and CT Images," International Journal, 2002, pp. 180-181.
Groom et al., "Robot-assisted transnasal laryngoplasty in cadaveric models: Quantifying forces and identifying challenges," The Laryngoscope, vol. e-pub ahea, p. n/a-n/a, 2015.
Haga et al., "Microsystems for minimally invasive medicine and healthcare," 2014 International Conference on Electronics Packaging, ICEP 2014, pp. 353-356, 2014.
Haque et al., "A slice based technique for low-complexity 3D/2D registration of CT to single plane x-ray fluoroscopy," 2012 International Conference on Digital Image Computing Techniques and Applications, DICTA 2012, pp. 1-6, 2012.

(56) References Cited

OTHER PUBLICATIONS

Harmon et al., "Time is Brain: The Future for Acute Ischemic Stroke Management is the Utilization of Steerable Microcatheters for Reperfusion," Cureus, vol. 11, No. 1, pp. 1-12, 2019.

Harteveld et al., "Ex vivo vessel wall thickness measurements of the human circle of Willis using 7T MRI," Atherosclerosis, vol. 273, pp. 106-114, 2018.

Hauberg et al., "Unscented kalman filtering on riemannian manifolds," Journal of Mathematical Imaging and Vision, vol. 46, No. 1, pp. 103-120, 2013.

Hinrichs et al., "Coil embolization of reversed-curve hepatointestinal collaterals in radioembolization: potential solutions for a challenging task," Radiology Case Reports, vol. 12, No. 3, pp. 529-533, 2017.

Hoffmann et al., "Reconstruction method for curvilinear structures from two views," Medical Imaging 2013: Image-Guided Procedures, Robotic Interventions, and Modeling, 2013, vol. 8671, p. 86712F.

Hoffmann et al., "Semi-automatic Catheter Reconstruction from Two Views," pp. 584-591, 2012.

Holmes et al., "Interventional Cardiology and Acute Stroke Care Going Forward: JACC Review Topic of the Week," Journal of the American College of Cardiology, vol. 73, No. 12, pp. 1483-1490, 2019.

Hong et al., "Tracking a magnetically guided catheter with a single rotating Arm", IEEE International Conference on Robotics and Automation, 2015, pp. 618-623, 2015.

Hopkins et al., "Public Health Urgency Created by the Success of Mechanical Thrombectomy Studies in Stroke," Circulation, vol. 135, No. 13, pp. 1188-1190, 2017.

Hussain et al., "In defense of our patients," Journal of NeuroInterventional Surgery, vol. 9, No. 6, pp. 525-526, 2017.

International Preliminary Report on Patentability for Application No. PCT/US2020/051009 dated Mar. 15, 2022 (4 pages).

Janjic et al., "Sparse ultrasound image reconstruction from a shape-sensing single-element forward-looking catheter," IEEE Transactions on Biomedical Engineering, vol. 65, No. 10, pp. 2210-2218, 2018.

Jovin et al., "Thrombectomy within 8 Hours after Symptom Onset in Ischemic Stroke," New England Journal of Medicine, vol. 372, No. 24, pp. 2296-2306, 2015.

Kapoor et al., "Suturing in Confined Spaces: Constrained Motion Control of a Hybrid 8-DoF Robot", IEEE International Conference on Advanced Robotics, 2005, 8 pages.

Kapoor et al., "Telemanipulation of Snake-Like Robots for Minimally Invasive Surgery of the Upper Airway," in MICCAI 2006 workshop on medical robotics, 2006.

Kerber et al., "Transparent Elastic Arterial Models I: A Brief Technical Note", Biorheology, No. 26, pp. 1041-1049, 1989.

Kim et al., "Development of a magnetic catheter with rotating multi-magnets to achieve unclogging motions with enhanced steering capability," AIP Advances, vol. 8, No. 5, 2018.

Knecht et al., "Computed tomography-fluoroscopy overlay evaluation during catheter ablation of left atrial arrhythmia," Europace, vol. 10, No. 8, pp. 931-938, 2008.

Knox et al., "Stereolithographic vascular replicas from CT scans: Choosing treatment strategies, teaching, and research from live patient scan data," American Journal of Neuroradiology, vol. 26, No. 6, pp. 1428-1431, 2005.

Kugelstadt et al., "Position and Orientation Based Cosserat Rods," In symposium on computer animation, vol. Jul. 11, pp. 169-178, 2016.

Kunz et al., "Lifetime quality of life and cost consequences of treatment delays in endovascular thrombectomy for stroke based on hermes data," Journal of NeuroInterventional Surgery, 2018, vol. 10, No. Suppl 2, pp. A1-A146.

Lima et al., "Prognosis of Untreated Strokes Due to Anterior Circulation Proximal Intracranial Arterial Occlusions Detected by Use of Computed Tomography Angiography," JAMA Neurology, vol. 71, No. 2, p. 151, 2014.

Marien et al., "Surgeon Resection Performance during Transurethral Resection of Bladder Tumor (TURBT): a Quantified Study," in 30th Annual Meeting of the Engineering & Urology Society, 2015, p. 25.

Marks et al., "Endovascular Treatment in the DEFUSE 3 Study," Stroke, vol. 49, No. 8, pp. 2000-2003, 2018.

Martin et al., "Welcome to the New Era: A Completely Wireless Interventional Procedure," Cureus, vol. 10, No. 9, 2018.

Meagher et al., "Anatomical flow phantoms of the nonplanar carotid bifurcation, Part II: Experimental validation with Doppler ultrasound," Ultrasound in Medicine and Biology, vol. 33, No. 2, pp. 303-310, 2007.

Mistretta, "Sub-Nyquist acquisition and constrained reconstruction in time resolved angiography," Medical Physics, vol. 38, No. 6, pp. 2975-2985, 2011.

Mistry et al., "Mechanical Thrombectomy Outcomes With and Without Intravenous Thrombolysis in Stroke Patients," Stroke, vol. 48, No. 9, pp. 2450-2456, 2017.

Mocco et al., "Aspiration Thrombectomy After Intravenous Alteplase Versus Intravenous Alteplase Alone", Stroke, 2016, vol. 47, No. 9, pp. 2331-2338.

Moghari et al., "Point-based rigid-body registration using an unscented Kalman filter," IEEE Transactions on Medical Imaging, vol. 26, No. 12, pp. 1708-1728, 2007.

Mueller-Kronast et al., "Systematic evaluation of patients treated with neurothrombectomy devices for acute ischemic stroke primary results of the STRATIS registry," Stroke, vol. 48, No. 10, pp. 2760-2768, 2017.

Muir et al., "Endovascular therapy for acute ischaemic stroke: The Pragmatic Ischaemic Stroke Thrombectomy Evaluation (PISTE) randomised, controlled trial," Journal of Neurology, Neurosurgery and Psychiatry, vol. 88, No. 1, pp. 38-44, 2017.

Nishihara, "Embolization of post-EVAR type II endoleaks," Case Report vol. 2., 2017, 4 pages.

Nogueira et al., "Thrombectomy 6 to 24 Hours after Stroke with a Mismatch between Deficit and Infarct," New England Journal of Medicine, p. NEJMoa1706442, 2017.

Nölker et al., "Novel robotic catheter manipulation system integrated with remote magnetic navigation for fully remote ablation of atrial tachyarrhythmias: A two-centre evaluation," Europace, vol. 14, No. 12, pp. 1715-1718, 2012.

Oliver-Butler et al., "Concentric agonist-antagonist robots for minimally invasive surgeries", 2017, vol. 10135, p. 1013511.

Owji et al., "Robotic-Assisted Inferior Vena Cava Filter Retrieval," Methodist DeBakey Cardiovascular Journal, vol. 13, No. 1, pp. 34-36, 2017.

Pennec et al., "A Framework for Uncertainty and Validation of 3-D Registration Methods based on Points and Frames," International Journal of Computer Vision, vol. 25, No. 3, pp. 203-229, 1997.

Perera et al., "Robotic Arch Catheter Placement Reduces Cerebral Embolization During Thoracic Endovascular Aortic Repair (TEVAR)," European Journal of Vascular and Endovascular Surgery, vol. 53, No. 3, pp. 362-369, 2017.

Pile et al., "Algorithms and design considerations for robot assisted insertion of perimodiolar electrode arrays," in Proceedings—IEEE International Conference on Robotics and Automation, 2011, pp. 2898-2904.

Powers et al., "2018 Guidelines for the Early Management of Patients With Acute Ischemic Stroke: A Guideline for Healthcare Professionals" From the American Heart Association/American Stroke Association, vol. 49, No. 3. 2018.

Rafii-Tari et al., "Current and emerging robot-assisted endovascular catheterization technologies: a review.," Annals of biomedical engineering, vol. 42, No. 4, pp. 697-715, 2014.

Rai et al., "A population-based incidence of acute large vessel occlusions and thrombectomy eligible patients indicates significant potential for growth of endovascular stroke therapy in the USA," Journal of NeuroInterventional Surgery, vol. 9, No. 8, pp. 722-726, 2017.

Rajsic et al., "Economic burden of stroke: a systematic review on post-stroke care," The European Journal of Health Economics, 2018, 29 pages.

Renda et al., "Discrete Cosserat Approach for Multi-Section Soft Robots Dynamics," p. 1, 2016.

(56) References Cited

OTHER PUBLICATIONS

Romesser et al., "Percutaneous Endoscopic Gastrostomy in Oropharyngeal Cancer Patients Treatred With Intensity-Modulated Radiotherapy With Concurrent Chemotherapy," Cancer, pp. 6072-6078, 2026.
Riga et al., "Robot-assisted fenestrated endovascular aneurysm repair (FEVAR) using the magellan system," Journal of Vascular and Interventional Radiology, vol. 24, No. 2, pp. 191-196, 2013.
Rone et al., "Continuum robot dynamics utilizing the principle of virtual power," IEEE Transactions on Robotics, vol. 30, No. 1, pp. 275-287, 2014.
Rosen et al., "SE-Sync: A certifiably correct algorithm for synchronization over the special Euclidean group," International Journal of Robotics Research, vol. 38, No. 2-3, pp. 95-125, 2019.
Rucker et al., "A geometrically exact model for externally loaded concentric-tube continuum robots," IEEE Transactions on Robotics, vol. 26, No. 5, pp. 769-780, 2010.
Rucker et al., "A model for concentric tube continuum robots under applied wrenches," Proceedings—IEEE International Conference on Robotics and Automation, pp. 1047-1052, 2010.
Saliba et al., "Atrial Fibrillation Ablation Using a Robotic Catheter Remote Control System. Initial Human Experience and Long-Term Follow-Up Results," Journal of the American College of Cardiology, vol. 51, No. 25, pp. 2407-2411, 2008.
Saliba et al., "Novel Robotic Catheter Remote Control System : Feasibility and Safety of Transseptal Puncture and Endocardial Catheter Navigation," Journal of Cardiovascular Electrophysiology, vol. 17, pp. 1102-1105, 2006.
Santa et al., "Intravascular microcatheter steered by conducting polymer actuators," International Conference of the IEEE Engineering in Medicine and Biology Society, pp. 2203-2204, 1996.
Sarli et al., "A Resectoscope for Robot-Assisted Transurethral Surgery 1," Journal of Medical Devices, vol. 10, No. 2, p. 020911, 2016.
Sarli et al., "Characterization of resection dexterity in transurethral resection of bladder tumor: A kinematic study," in 2015 IEEE International Conference on Robotics and Automation (ICRA), 2015, pp. 5324-5329.
Sarli et al., "Kinematic and experimental investigation of manual resection tools for transurethral bladder tumor resection," The International Journal of Medical Robotics and Computer Assisted Surgery, vol. 13, No. 2, p. e1757, 2017.
Sarli et al., "Minimal visual occlusion redundancy resolution of continuum robots in confined spaces," in 2017 IEEE/RSJ International Conference on Intelligent Robots and Systems (IROS), 2017, pp. 6448-6454.
Sarli et al., "Preliminary Porcine in vivo Evaluation of a Telerobotic System for Transurethral Bladder Tumor Resection & Surveillance," Journal of Endourology, p. end.2018.0119, Mar. 2018.
Saver et al., "Stent-Retriever Thrombectomy after Intravenous t-PA vs. t-PA Alone in Stroke," New England Journal of Medicine, vol. 372, No. 24, pp. 2285-2295, 2015.
Schenderlein et al., "Catheter tracking in asynchronous biplane fluoroscopy images by 3D B-snakes", Medical Imaging 2010: Visualization, Image-Guided Procedures, and Modeling, 2010, vol. 7625, p. 76251U.
Searbury et al., "Regional disparities in the quality of stroke care," American Journal of Emergency Medicine, vol. 35, No. 9, pp. 1234-1239, 2017.
Shaikh et al., "The AmigoTM Remote Catheter System: From Concept to Bedside," The Journal of Innovations in Cardiac Rhythm Management, vol. 8, No. 8, pp. 2795-2802, 2017.
Simaan et al., "A dexterous system for laryngeal surgery", IEEE ICRA, 2004, pp. 351-357.
Simaan et al., "Lessons learned using the insertable robotic effector platform (IREP) for single port access surgery," Journal of Robotic Surgery, vol. 7, No. 3, pp. 235-240, 2013.
Simaan, "Snake-like units using flexible backbones and actuation redundancy for enhanced miniaturization," Proceedings—IEEE International Conference on Robotics and Automation, 2005, pp. 3012-3017.
Small IV et al., "Prototype fabrication and preliminary In Vitro testing of a shape memory endovascular thrombectomy device," IEEE Transactions on Biomedical Engineering, vol. 54, No. 9, pp. 1657-1666, 2007.
Soyama et al., "The Steerable Microcatheter: A New Device for Selective Catheterisation," CardioVascular and Interventional Radiology, vol. 40, No. 6, pp. 947-952, 2017.
Srivatsan et al., "Estimating SE(3) elements using a dual quaternion based linear Kalman filter," Robotics: Science and Systems, vol. 10, 2016, 10 pages.
Srivatsan et al., "Probabilistic pose estimation using a Bingham distribution-based linear filter," International Journal of Robotics Research, vol. 37, No. 13-14, pp. 1610-1631, 2018.
Till et al., "Efficient Computation of Multiple Coupled Cosserat Rod Models for Real-Time Simulation and Control of Parallel Continuum Manipulators," pp. 5067-5074, 2015.
Vernikouskaya et al., "Improved Registration of 3D CT Angiography with X-ray Fluoroscopy for Image Fusion During Transcatheter Aortic Valve Implantation," Journal of Visualized Experiments, No. 136, pp. 2-7, 2018.
Vuong et al., "Application of emerging technologies to improve access to ischemic stroke care | Neurosurgical Focus," Neurosurgical Focus, vol. 42, No. 4, p. E8, 2017.
Wagner et al., "4D interventional device reconstruction from biplane fluoroscopy," Medical Physics, vol. 43, No. 3, pp. 1324-1334, 2016.
Walters et al., "Robotic-Assisted Percutaneous Coronary Intervention: Concept, Data, and Clinical Application," Interventional Cardiology Clinics, vol. 8, No. 2. Elsevier Inc, pp. 149-159, 2019.
Webster III et al., "Statics and Dynamics of Continuum Robots With General Tendon Routing and External Loading," IEEE Transactions on Robotics, vol. 27, No. 6, pp. 1033-1044, 2011.
Wei et al., "Modeling, Force Sensing, and Control of Flexible Cannulas for Microstent Delivery," Journal of Dynamic Systems, Measurement, and Control, vol. 134, No. 4, p. 041004, 2012.
White, "Acute Stroke Intervention: The Role of Interventional Cardiologists," Journal of the American College of Cardiology, vol. 73, No. 12, pp. 1491-1493, 2019.
Xu et al., "A fast torsionally compliant kinematic model of concentric-tube robots," Proceedings of the Annual International Conference of the IEEE Engineering in Medicine and Biology Society, EMBS, pp. 904-907, 2012.
Xu et al., "Actuation Compensation for Flexible Surgical Snake-like Robots with Redundant Remote Actuation," in IEEE International Conference on Robotics and Automation, 2006, pp. 4148-4154.
Xu et al., "An investigation of the intrinsic force sensing capabilities of continuum robots," IEEE Transactions on Robotics, vol. 24, No. 3, pp. 576-587, 2008.
Xu et al., "Analytic Formulation for Kinematics, Statics, and Shape Restoration of Multibackbone Continuum Robots Via Elliptic Integrals," Journal of Mechanisms and Robotics, vol. 2, No. 1, p. 011006, 2010.
Xu et al., "Intrinsic Wrench Estimation and Its Performance Index for Multisegment Continuum Robots," IEEE Transactions on Robotics, vol. 26, No. 3, pp. 555-561, 2010.
Simaan et al., "Nabil Simaan Design and Integration of a Telerobotic System for Minimally Invasive Surgery of the Throat," The International Journal of Robotics Research, vol. 28, No. 9, pp. 1134-1153, 2009.
Xu, "Design, Modeling and Analysis of Continuum Robots as Surgical Assistants with Intrinsic Sensory Capabilities," Ph.D. Dissertation, Mechanical Engineering, Columbia University, 2009.
Yi et al., "Predictors of false-positive stroke thrombectomy transfers," Journal of NeuroInterventional Surgery, vol. 9, No. 9, pp. 834-836, 2017.
Zaidat et al., "Impact of Balloon Guide Catheter Use on Clinical and Angiographic Outcomes in the STRATIS Stroke Thrombectomy Registry," Stroke, vol. 50, No. 3, pp. 697-704, 2019.

(56) References Cited

OTHER PUBLICATIONS

Zhang et al., "A pilot study of robot-assisted cochlear implant surgery using steerable electrode arrays", Med. Image Comput. Assist. Interv., 2006, vol. 9, pp. 33-40.

Zhang et al., "Design of Underactuated Steerable Electrode Arrays for Optimal Insertions," Journal of Mechanisms and Robotics, vol. 5, No. 1, p. 011008, Jan. 2013.

Zhang et al., "Inroads Toward Robot-Assisted Cochlear Implant Surgery Using Steerable Electrode Arrays," Otology & Neurotology, vol. 31, No. 8, pp. 1199-1206, Jun. 2010.

Zhang et al., "Model and parameter identification of friction during robotic insertion of cochlear-implant electrode arrays," in 2009 IEEE International Conference on Robotics and Automation, 2009, pp. 3859-3864.

Zhang et al., "Optimal Path Planning for Robotic Insertion of Steerable Electrode Arrays in Cochlear Implant Surgery," Journal of Medical Devices, vol. 3, No. 1, pp. 011001-1-011001-10, 2009.

Zhang et al., "Path planning and workspace determination for robot-assisted insertion of steerable electrode arrays for cochlear implant surgery", Proceedings of the 11th International Conference on Medical Image Computing and Computer-Assisted Intervention, 2008, vol. 5242, pp. 692-700.

Zhang, "Design of Steerable Electrode Arrays and Optimal Insertion Path Planning for Robot-Assisted Cochlear Implant Surgery," Columbia University, 2010, 222 pages.

Zheng et al., "A Class of Novel Point Similarity Measures Based on MAP-MRF Framework for 2D-3D Registation of X-Ray Fluoroscopy to CT Images," 3rd IEEE International Symposium on Biomedical Imaging: Nano to Macro, 2006., pp. 438-441.

Zollei et al., "2D-3D rigid registration of X-ray fluoroscopy and CT images using mutual information and sparsely sampled histogram estimators," IEEE, pp. II-696-II-703, 2001.

Puri, "Trevo Aspiration Proximal Flow Control Registry, Stryker Neurovascular," Clinical Trial, 2019, <https://clinicaltrials.gov/ct2/show/NCT03199404>, 7 pages.

Auris, "Monarch Platform—Endoscopy Transformed", Product Information, <https://www.aurishealth.com/monarch-platform>, Accessed: May 29, 2019, 7 pages.

Philips, "Corindus CorPath® 200—Robotic-assisted PCI system", Product Information, <https://www.philips.com.sg/healthcare/product/HC722362/corindus-corpath-200-robotic-assisted-pci>, 2013, 4 pages.

Merit Medical, "SwiftNINJA Steerable Microcatheter", Product Information, <https://www.merit.com/interventional-oncology-spine/accessories/microcatheters/swiftninja-steerable-microcatheter/>, accessed: May 29, 2019, 8 pages.

Bendit, "Technology—Bendit Technologies", <https://www.bendittech.com/technology/>, Accessed: May 29, 2019, 5 pages.

"Titan Medical Inc. Enters Into Exclusive License Agreement with Columbia University for Novel Single Port Robotic Surgery System", Feb. 2012, <https://www.benzinga.com/pressreleases/12/02/m2345785/titan-medical-inc-enters-into-exclusive-license-agreement-with-columbia>, 6 pages.

International Search Report and Written Opinion, PCT/US2020/051009, dated Dec. 7, 2020. 5 pages.

\* cited by examiner

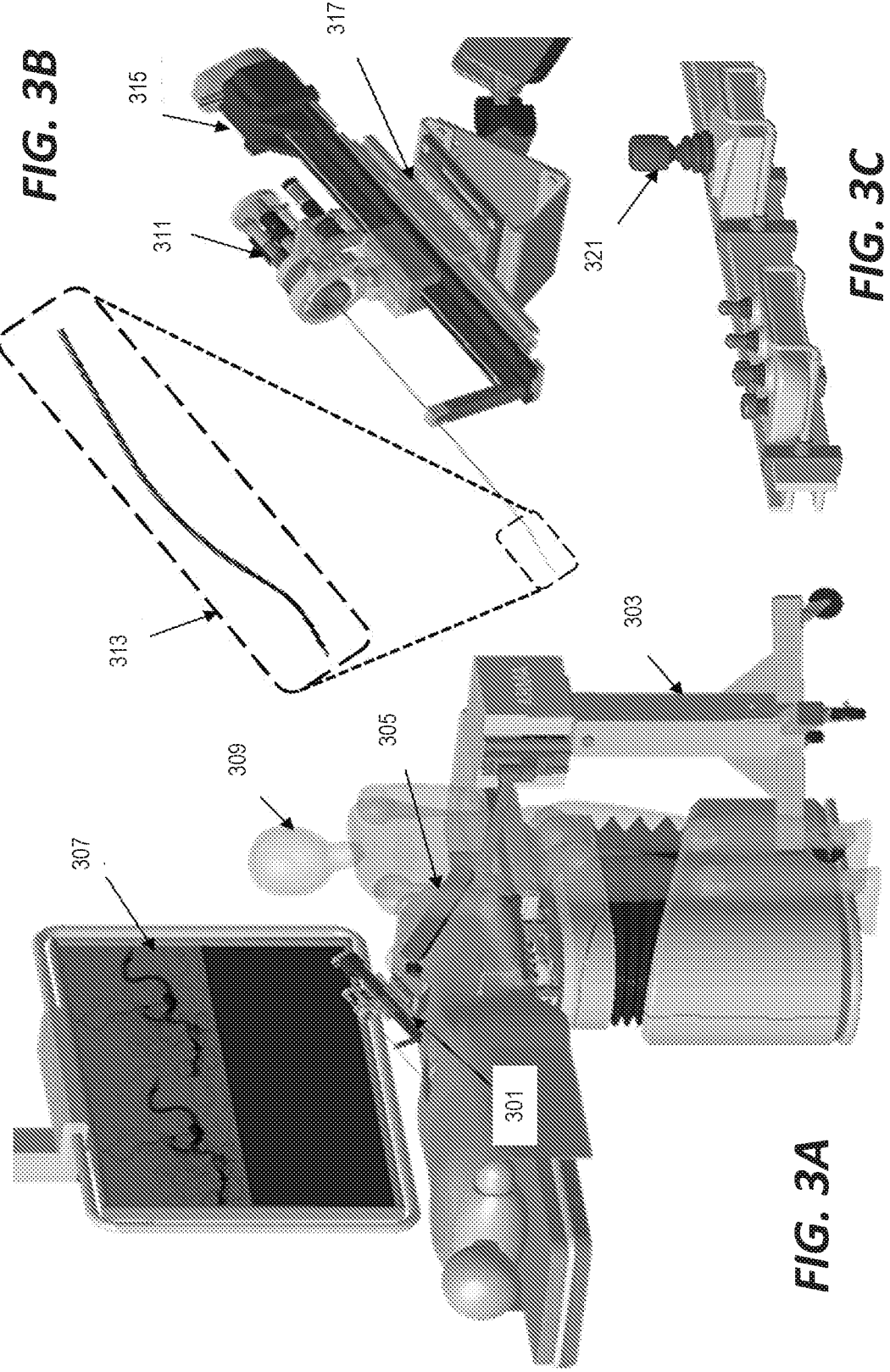

MULTI-ARTICULATED CATHETERS WITH SAFETY METHODS AND SYSTEMS FOR IMAGE-GUIDED COLLABORATIVE INTRAVASCULAR DEPLOYMENT

RELATED APPLICATIONS

This Patent Application is the U.S. national stage entry, under 35 U.S.C. § 371, of International Application Number PCT/US2020/051009, filed Sep. 16, 2020, which claims the benefit of U.S. Provisional Application No. 62/901,114, filed Sep. 16, 2019, entitled "SMART MULTI-ARTICULATED CATHETERS WITH SAFETY METHODS AND SYSTEMS FOR IMAGE-GUIDED COLLABORATIVE INTRAVASCULAR DEPLOYMENT," the entire contents of each of which are incorporated herein by reference.

BACKGROUND

The present invention relates to systems and devices for safety, deployment, and articulation of catheters including, for example, micro-catheters.

SUMMARY

In one embodiment, the invention provides a robotic catheter system including an actuator, a sensor, and an electronic controller. The actuator includes an active linear movement stage, a motor, and a spring. The motor is coupled to the active linear movement stage and configured to control linear movement of the active linear movement stage in response to a control signal. The spring couples the active linear movement stage to a control backbone of a robotic catheter and is configured to transfer linear movement from the linear movement stage to the control backbone. Linear movement of the control backbone causes a controllable bending of the robotic catheter. The sensor is configured to monitor a spring deflection of the spring. The electronic controller is configured to generate a control signal to control the bending of the catheter based at least in part on the spring deflection signal from the sensor.

In some embodiments, the spring allows a bending movement of the robotic catheter due to an external force applied to the robotic catheter without movement of the active linear movement stage. Conversely, in some embodiments, the spring allows an external force applied to the robotic catheter to limit a bending movement of the robotic catheter caused by movement of the active linear movement stage.

In some embodiments, the invention provides a system for operating an articulating micro-catheter that uses image-guidance with several assistive modes and with device embodiments allowing manual insertion, steering via joystick and collaborative control with virtual fixtures. In some embodiments, a virtual fixture is an assistive control law implemented by the system that assists the robot user in achieving a certain manipulation task such as, for example, limiting movement of a robotic device to within the boundaries of a defined virtual fixture.

In another embodiment, the invention provides a smart catheter that has the ability to actively steer and also to go "limp" when needed. In some embodiments, the micro-catheter includes multi-articulated segments. In yet another embodiment, the invention provides a steerable device that enable catheters to more easily navigate by using a deployable steerable tip. In still another embodiment, the invention provides systems and methods for enhanced traction for removal of clots using a side window.

Some embodiments provide one or more of the following: (i) steerable devices for intracranial intervention (stroke treatment, aneurysm treatment, arterio-venous malformation treatment, arterio-venous fistula treatment, tumor embolization, etc.), (ii) steerable devices for inspection of coiling channels/ducts in cast parts, and (iii) steerable devices for intravascular intervention (e.g., intracardiac ablation).

Other aspects of the invention will become apparent by consideration of the detailed description and accompanying drawings.

BRIEF DESCRIPTION OF THE DRAWINGS

FIG. 3A is a perspective view of a system for operating the articulatable catheter of FIG. 1 in use.

FIG. 3B is a perspective view of an actuator unit for the articulatable catheter in the system of FIG. 3A.

FIG. 3C is a perspective view of a user control for the system of FIG. 3A.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
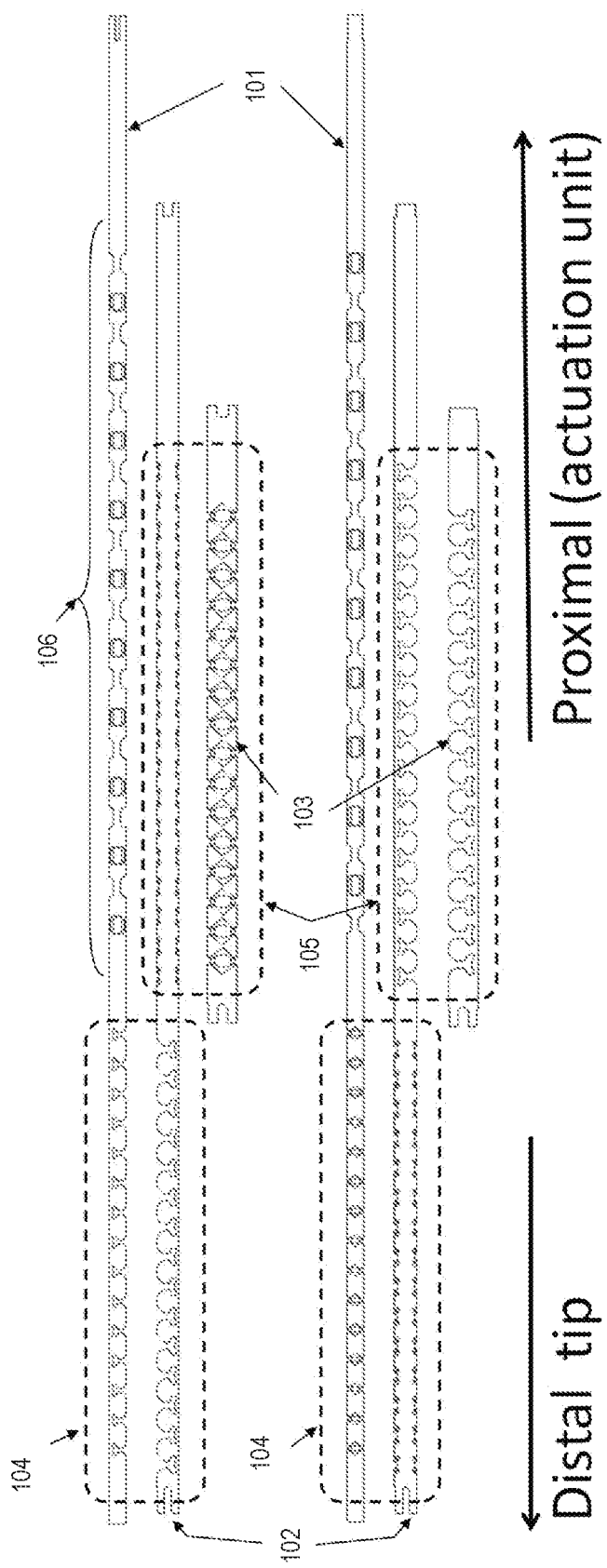
FIG. 1 is an exploded view from two different perspectives of a catheter configured for active articulation and passive articulation in accordance with one embodiment.

FIG. 1 illustrates one example of a catheter configured for both passive articulation and active/controlled articulation where the active/controlled articulation is provided by applying a pushing/pulling force on a proximal end of the catheter. This particular design uses antagonistic pulling and pushing on concentric tubes with eccentric flexures to achieve a controlled bending of the catheter body. Three thin-walled, super-elastic NiTi tubes (i.e., an inner tube 101, an intermediate tube 102, and an outer tube 103) are micro-machined using electron discharge machining or femtosecond laser to create a series of flexures designed in a specific way to reduce flexural rigidity.

The inner tube 101 serves as a main support for the catheter and is proximally notched with bidirectionally alternating flexures 106 that reduce its flexural rigidity so that the inner tube 101 acts as a passively bending microcatheter in its proximal portion. The distal tip of this inner tube 101 has a different flexure pattern consistent with forming an antagonistic bending segment 104 with the intermediate tube 102. The intermediate tube 102 is concentrically arranged around the inner tube 101 and fixedly coupled to the inner tube 101 at their distal ends. By pushing/pulling the inner tube 101 relative to the intermediate tube 102 (e.g., pushing/pulling the inner tube 101 while the intermediate tube 102 is fixedly coupled to the base of the actuation unit), the distal bending segment 104 of the catheter is controllably bent.

The outer tube 103 is concentrically arranged around both the inner tube 101 and the intermediate tube 102. The outer tube 103 in the example of FIG. 1 has a shorter length than the inner tube 101 and the intermediate tube 102 and the distal end of the outer tube 103 is fixedly coupled to the intermediate tube 102. Flexure patterns are formed in the outer tube 103 and the portion of the intermediate tube 102 that is surrounded by the outer tube 103 in order to provide another antagonistic bending segment 105 in the catheter. Similar to the operation of the distal bending segment 104, by pushing/pulling the outer tube 103 relative to the intermediate tube 102, the proximal bending segment 105 of the catheter is controllably bent.

In the example of FIG. 1, the flexure patterns in the distal bending segment 104 and the proximal bending segment 105 are angularly offset so that the distal tip of the catheter can be positioned in 3D space by controllable bending of the catheter (i.e., with two degrees-of-freedom). Also, in the example of FIG. 1, the alternating flexures 106 extended further along the inner tube 101 towards the proximal end of the catheter than the proximal bending segment 105. Accordingly, in some implementations, the catheter is configured to provide actively-controlled bending nearer to its distal tip and to provide passive bending nearer to its proximate end.

Figure 2:
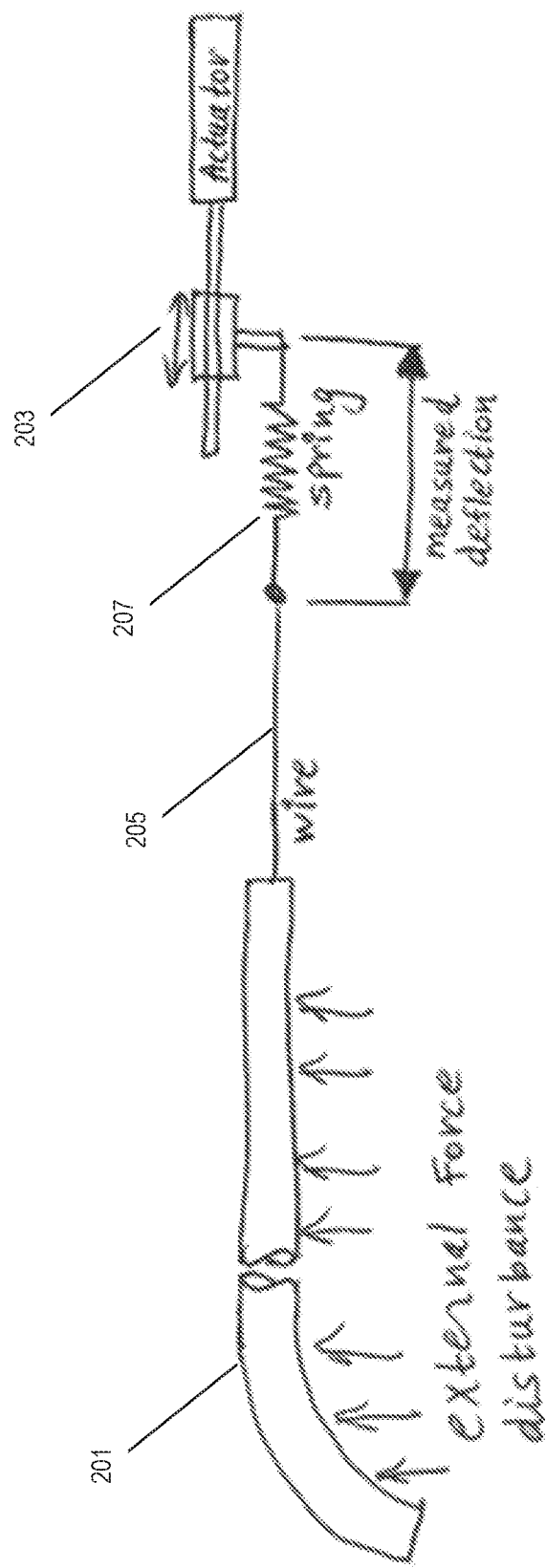
FIG. 2 is a schematic diagram of a system for controlling the articulation of the catheter of FIG. 1 with a passive safety mechanism.

FIG. 2 illustrates an example of a system for controlling the active bending of a catheter using series-elastic actuation. Although the system of FIG. 2 is described in reference to the catheter of FIG. 1, the series-elastic actuation functionality can also be adapted for use in other types of articulatable catheters (for example, continuum robots in which bending of segments is controlled by pushing/pulling individual "backbones"). This series-elastic actuation provides for fault tolerance, increases safety, and allows force sensing at the catheter tip.

In the example of FIG. 2, each controllable "backbone" of the catheter 201 (i.e., the tubes, wires, etc. In the catheter to which a linear push-pull force is applied in order to control the active bending of the catheter) is coupled to an actuator 203 that applies a linear push/pull force to the backbone. Each backbone of the catheter 201 is coupled—either directly or indirectly (e.g., by a wire 205) to a precision calibrated spring 207 that is supported on a linear ball bearing (not pictured). The opposite end of the spring 207 is coupled to the actuator 203. In this manner, the pushing/pulling force is applied to the backbone of the catheter 201 by the actuator 203 through the spring 207.

As discussed further below, the spring provides an additional passive safety mechanism for unintended bending forces applied to the catheter, for example, due to contact between the catheter and an internal anatomical structure when the device is operated in a human body. Also, deflection of the spring is monitored by a controller and used as an input for the active bending control of the catheter (as also discussed in further detail below). Although the examples described herein refer primary to a spring 207, other elastic elements might be utilized in other implementations including, for example, elastomers, programmable electromechanical devices such as voice coil actuators, or other electromechanical actuators that have their own controller to make them behave as a spring.

Figure 3D:
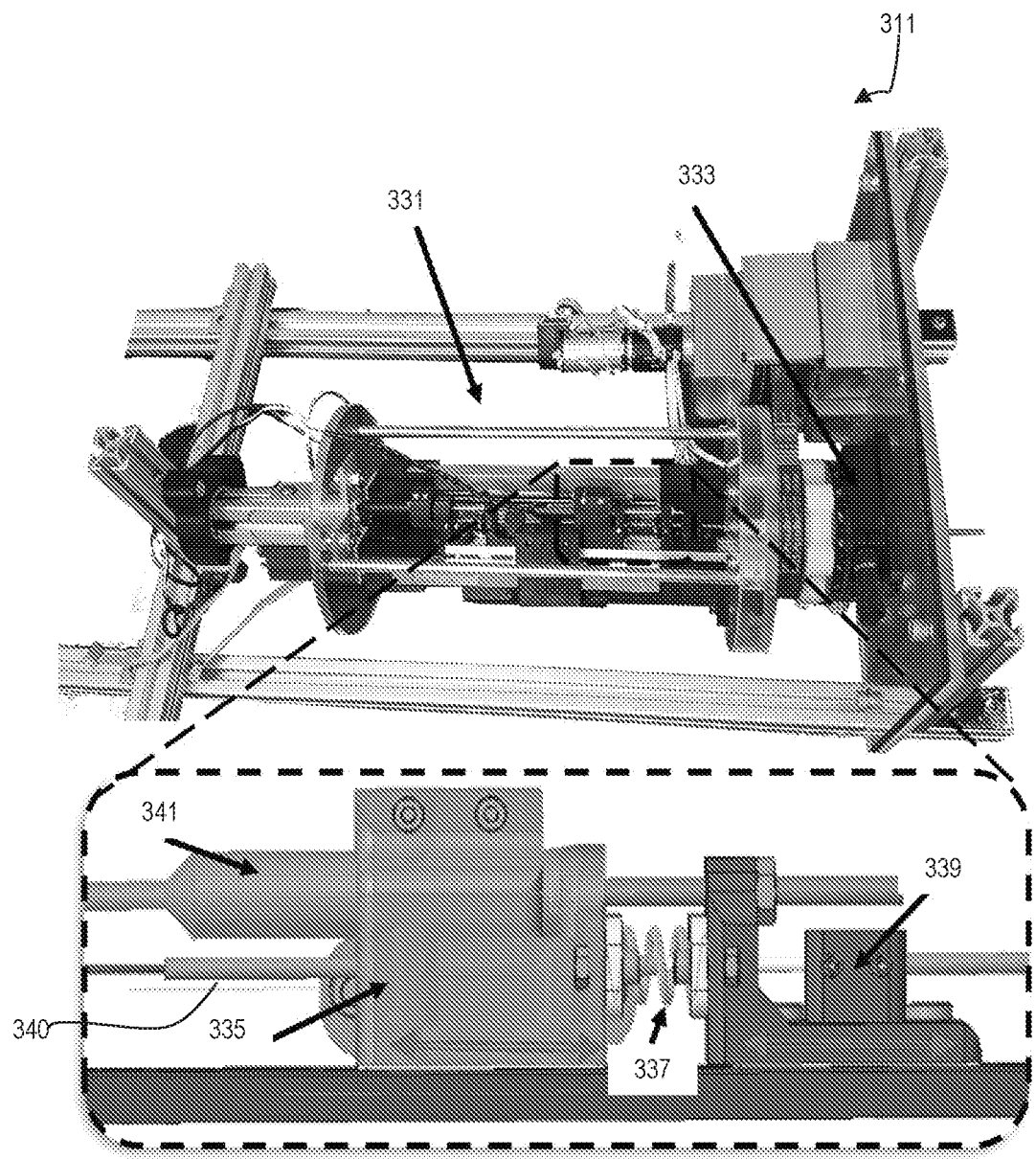
FIG. 3D is a perspective view of the actuator of FIG. 3B.

FIGS. 3A through 3D illustrate further details of the catheter actuator and an example of the catheter system in use by a medical professional. As shown in FIG. 3A, a catheter insertion robot 301 is coupled to a movable cart 303 by a statically balanced arm 205. A fluoroscopic imaging system 307 is positioned to capture image data of a patient and of the catheter inserted into the patient's anatomy. Image data from the fluoroscopic imaging system 307 and other information is displayed on a screen that can be viewed by the medical professional 309 operating the system. As shown in further detail in FIG. 3C, one or more user controls (e.g., a joystick 321) is positioned on the patient table in order to receive user input commands from the medical professional 309. Although the joystick 321 is shown attached to the patient bed in the example of FIGS. 3A and 3C, the user controls may be positioned elsewhere (e.g., attached to the movable cart 303) in other implementations.

FIG. 3C illustrates the catheter insertion robot 301 in further detail. An actuation unit 311 is coupled to the catheter 313 to apply bending force to the catheter 313. The actuation unit 311 is also coupled to an insertion stage 315 configured to advance and retract the catheter 313 by controllably altering a linear position of the actuator unit 311. The insertion stage 315 (and, thereby, the actuation unit 311) is coupled to the distal end of the arm 305 by a quick connect interface 317 or another type of mounting bracket.

FIG. 3D illustrates the actuation unit 311 in further detail. The actuation unit 311 includes a catheter actuator 331 configured to apply bending forces to the catheter 313 and a rotary stage 333. The rotary stage 333 is configured to controllably rotate the catheter 313 by applying a rotating force to the catheter actuator 331. As shown in the insert in FIG. 3D, the catheter actuator includes an active carriage 335 that is coupled by a precision spring 337 to a free-floating carriage 339. A backbone 440 (e.g., one of the concentric tubes in the catheter of FIG. 1) extends through the active carriage 335 and is fixedly coupled to the free-floating carriage 339. To adjust the linear position of the backbone 440, the active carriage 335 is moved linearly by a motor. The spring 337 conveys this linear movement to the free-floating carriage 339 which, in turn, transfers the linear movement to the backbone 440.

The spring 337 allows for linear movement of the free-floating carriage 339 and the backbone 440 that does not exactly match the linear movement of the active carriage 335. As described in further detail below, this difference in linear movement provides an additional passive safety mechanism for the catheter 313. The difference in linear movement (i.e., the deflection of the spring) is also monitored and both motor-encoder feedback & the measured spring deflection are used to deduce the joint-level forces applied to the catheter 313 and to, in turn, control the active bending of the catheter 313. In the example of FIG. 3D, a high precision potentiometer 341 is configured to measure spring deflection by monitoring the distance between the active carriage 335 and the free-floating carriage 339.

Figure 4:
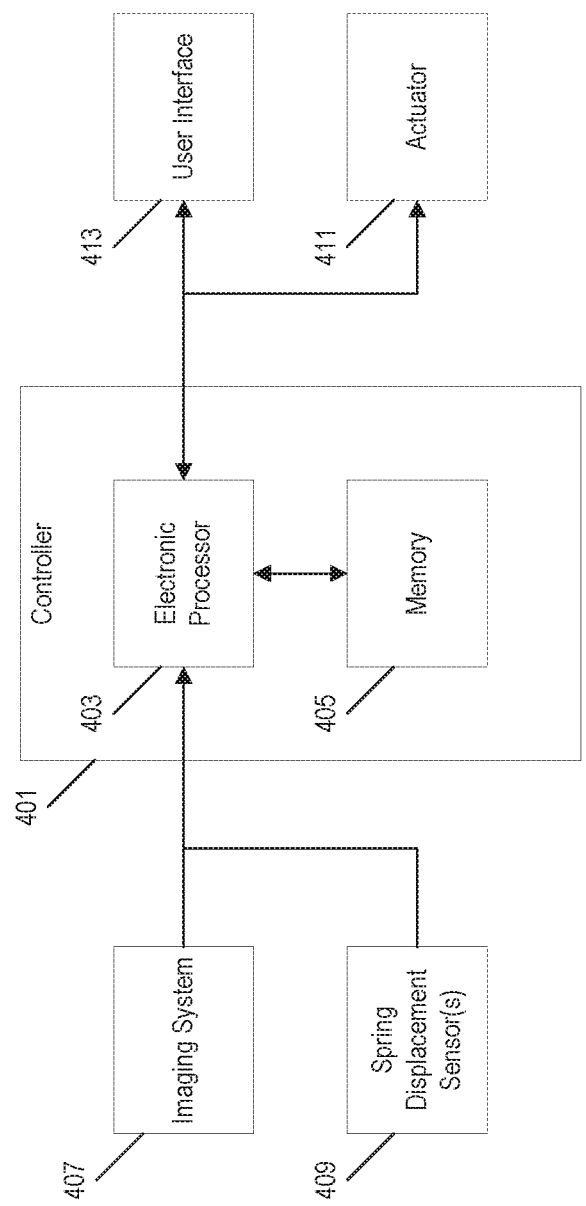
FIG. 4 is a block diagram of a control system for operating the articulatable catheter in the system of FIG. 3A.

FIG. 4 illustrates an example of a control system for operating the catheter actuator 331. A controller 401 includes an electronic processor 403 and a non-transitory, computer-readable memory 405. The memory 405 stores data and computer-executable instructions that are accessed and executed by the electronic processor 403 to provide the functionality of the controller 401. The controller 401 is communicatively coupled to an imaging system 407 (e.g., the fluoroscopic imaging system 307 of FIG. 3A), one or more spring displacement sensors 409 (e.g., the potentiometer 341), the catheter actuator 411 (e.g., the motors of the actuation unit 311), and a user interface 413 (e.g., the display screen of the imaging system 307 and the user input controls 321). When the system is used in medical applications for controlling the movement of the catheter within a patient's body, the image data received by the controller 401 from the imaging system 407 may include, for example, images of the internal anatomy of the patient and image data showing the catheter 313 positioned within the internal anatomy. However, although the examples described herein are related to the medical domain, it should be understood that there are other possible application domains where the systems and methods described herein might be applied including, for example, the inspection of cast parts (e.g., inspection of oil/cooling ducts in sand-cast components).

Figure 5:
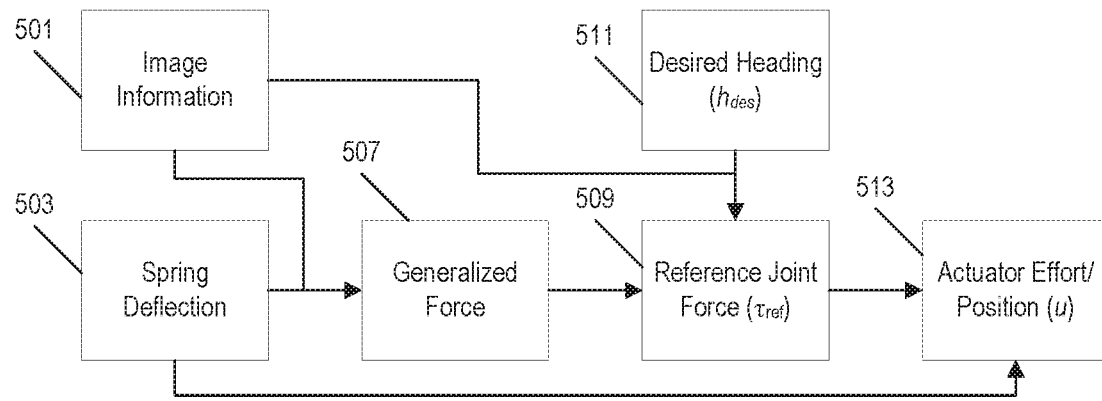
FIG. 5 is a flowchart of a method for controlling articulation of the catheter using the system of FIG. 4.

FIG. 5 illustrates an example of a method for controllably bending the catheter using the system of FIG. 4. In this example, image information 501 from the imaging system and the measured spring deflection 503 are used as control inputs for determining the position/force to be applied to a backbone by the actuator. Generalized force 507 is determined based on the image information 501 and the measured spring deflection 503. A desired heading ($h_{des}$) 511 is determined from image information showing the position of the catheter and the surrounding anatomical structure (e.g., from fluoroscopic image data). Based on the generalized force information 507 and the desired heading ($h_{des}$) 511, the controller 401 calculates a reference joint force ($\tau_{ref}$) 509. In some implementations, the reference joint force ($\tau_{ref}$) 509 is calculated using the equation:

$$\tau_{ref} = k_p \underbrace{(h_{cur} - h_{des})}_{e_h} + k_i \int (h_{cur} - h_{des}) dt \quad (1)$$

where $h_{cur}$ is the current heading of the catheter tip and eh is an error metric that captures deviation of the current catheter tip heading from the desired heading ($h_{cur}-h_{des}$).

A motor control signal (u) 513 is then determined by the controller 401 based on the calculated reference joint force ($\tau_{ref}$) 509 and the measured spring deflection 503 using the equation:

$$u = k_p(\tau_{cur} - \tau_{ref}) + k_i \int (\tau_{cur} - \tau_{ref}) dt \quad (2)$$

where $\tau_{cur}$ is the current joint force of the catheter and is determined based on the known position of the actuator (e.g., from motor encoder feedback from the motor driving the active carriage 335) (K) and the measured spring deflections (x) where $\tau_{cur} = Kx$.

In some implementations, Equation (2) is used to implement a proportional integrator law to cause the joint forces to converge on $\tau_{ref}$. In such cases, u is the motor control signal (e.g., the current if the motors are controlled in current mode or velocity if the motors are controlled in a velocity mode). In some implementations, u represents the "actuator effort" (e.g., current force) or position). If u is position, then it is assumed that there is a tertiary-level position controlled (e.g., PID position controller) for each joint.

Since the catheter will likely experience some twist from its point of entry to its distal tip, reliance on pre-operative path planning is not sufficient. Even though vessel anatomy does not change with the head of the patient fixed, the robot kinematic mapping does change and an added safety measure is needed to allow safe semi-automated navigation. Two tools that may be used to address this challenge include (1) a periodic Jacobian update using joint-level and image segmentation information, and (2) the use of joint level force sensing for updating the joint-level commands based on the nominal path plan. The periodic Jacobian update relies on numerical estimations of input-output mappings between joint motions from encoders and catheter bending from image segmentation. This approach may be augmented with use of joint-level force sensing and a static model of the catheter. If one simulates the catheter insertion along a nominal path plan, one expects a joint force level $\hat{\tau}$ for every given arc length along the path. A Jacobian of this force as a function of twist angle may be obtained through simulation on different twist angles while including the statics model of the robot as a predictor of the joint force expected value $\hat{\tau}$. Using a parametrization of this Jacobian (e.g. though Fourier series compression or though brute force look-up tables) one can estimate the twist angle. Finally, an ultimate safety check will be applied if the difference between $\hat{\tau}$ and $\tau_{cur}$ exceeds a threshold. This would be in the form of pausing insertion, applying a relaxation of joint forces through an active compliance law where $\tau_{ref}$ is set to $\hat{\tau}$ based on image segmentation data feeding into the statics model of the catheter. Once the error in joint level force is minimized within a threshold zone, automatic insertion may proceed with a correction term for $\tau_{ref}$ based on the output of the compliance control law.

Based on the general control mechanism illustrated in FIG. 5, the system in some implementations is configured to operate in three different control modes: Mode 1—Passive Compliance (FIG. 6), Mode 2—Active Compliance (FIG. 8), and Mode 3—User Steering (FIG. 9).

Figure 6:
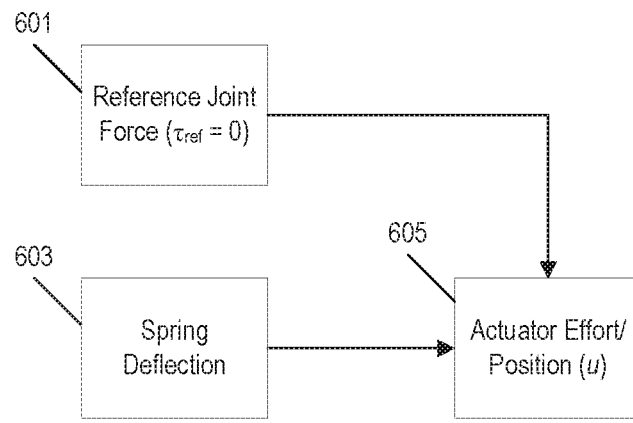
FIG. 6 is a flowchart of a method for controlling articulation of the catheter in a first mode of operation (i.e., Mode 1: Passive Compliance).

FIG. 6 illustrates an example of a method for implementing operation of the actuator system under Mode 1—Passive Compliance. In some implementations, this mode is used during the stage of manual insertion of the catheter tip. During this phase, the actuation unit is put in the passive compliance mode to protect the catheter tip from overloading of its backbones. The motor control signal u is calculated (step 605) using the control law of Equation (2) based on the measured spring deflection 603 and with $\tau_{ref}=0$ to allow the actuation unit to comply with disturbances due to the medical professional manually manipulating the catheter body.

Figure 7A:
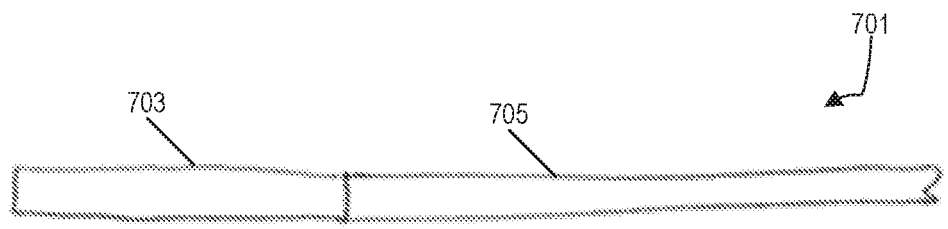
FIGS. 7A, 7B, and 7C are elevation views of the articulatable catheter demonstrating both active and passive articulation.
Figure 7B:
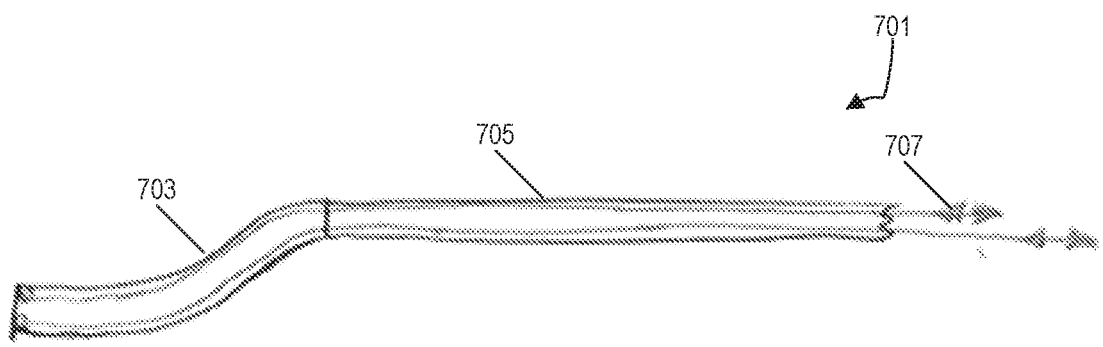
Figure 7C:
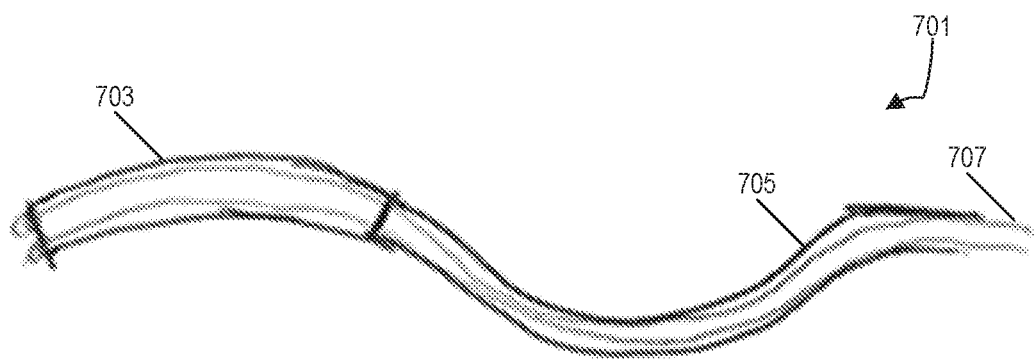

FIGS. 7A, 7B, and 7C illustrate an example of the problems involved with manual insertion of a robotic catheter that are addressed by the Mode 1 operation of FIG. 6. FIG. 7A shows a catheter 701 with an actively articulatable segment 703 and a passively articulatable segment 705. Again, although the example of FIG. 7A shows only one bending segment, it should be understood that the catheter 701 in other implementations may have multiple actively bending segments being actuated by wires or other means of mechanical actuation. FIG. 7B shows the same catheter 701 with the active segment 703 deflected due to an external load (applied by a push/pull force on backbones 707) while the passive segment 705 remains straight. However, in some implementations, the bending angle at the distal tip of the catheter does not depend on the shape of the actuated segment (i.e., if it is deflected under loading its tip will maintain its angle). In some such implementations, this phenomenon is due to circumferential placement of the actuation wires 707.

During manipulation by a medical professional, the passive segment 705 is likely to be bent. As shown in FIG. 7C, if an actuator such as illustrated in FIG. 3D is used to control the bending of the active segment, then bending of the passive segment 705 causes a corresponding bending of the active segment 703. In contrast, Mode 1 operation adjusts the actuation force applied to the backbones 707 by the actuator to enable the passive segment 705 to bend without causing a corresponding bending of the active segment 703. Accordingly, Mode 1 operation allows the catheter to "go limp" during insertion.

Also, in some implementations, Mode 1 operation allows deployment in a non-calibrated setting where, after deployment, a user can toggle Mode 1 to relax any internal forces in the system due to model discrepancy and lack of exact registration between the robot and the environment. In some implementations, Modes 2 & 3 (discussed below) may also allow periodic toggling into Mode 1 to address discrepancies in the model due to cumulative registration error. Such toggling will occur based on a state estimator or based on thresholding on spring deflection from expected values based on image segmentation of the catheter tip.

Figure 8:
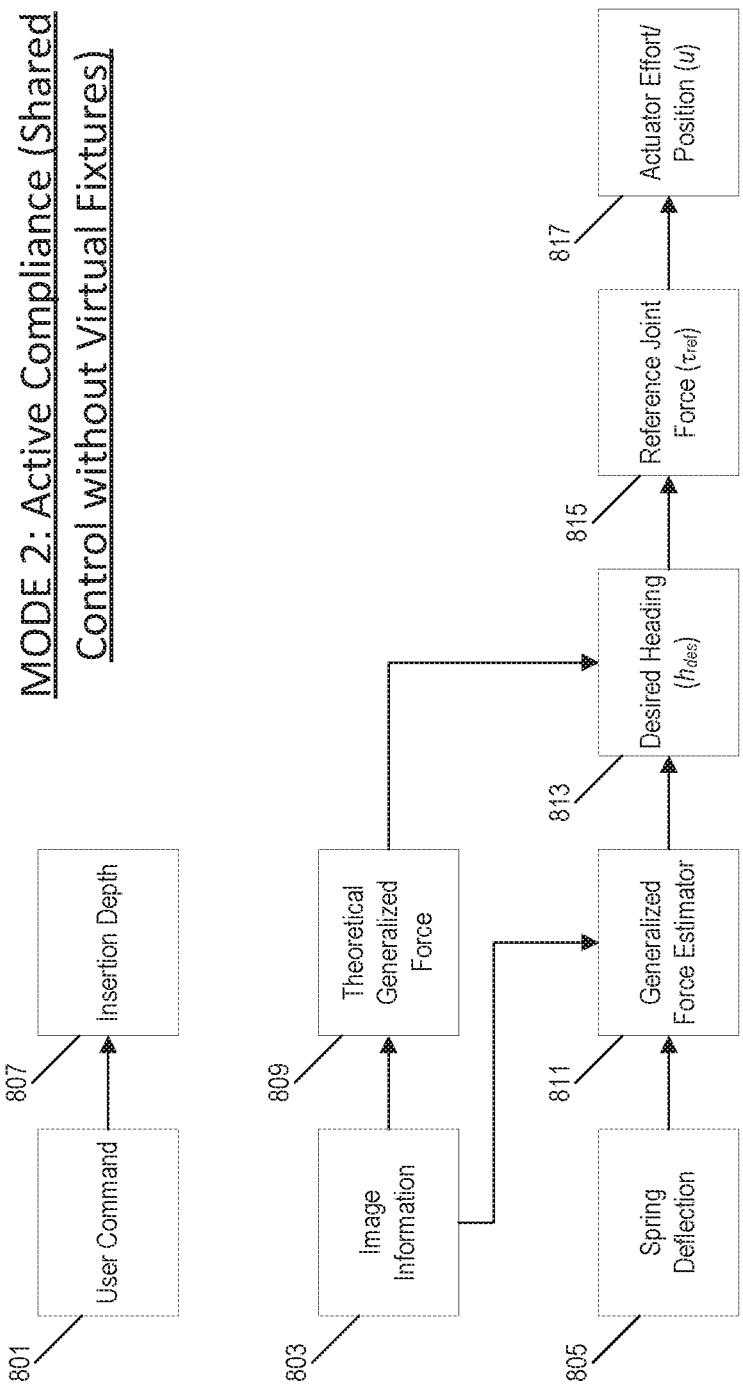
FIG. 8 is a flowchart of a method for controlling articulation of the catheter in a second mode of operation (i.e., Mode 2: Active Compliance).
Figure 9:
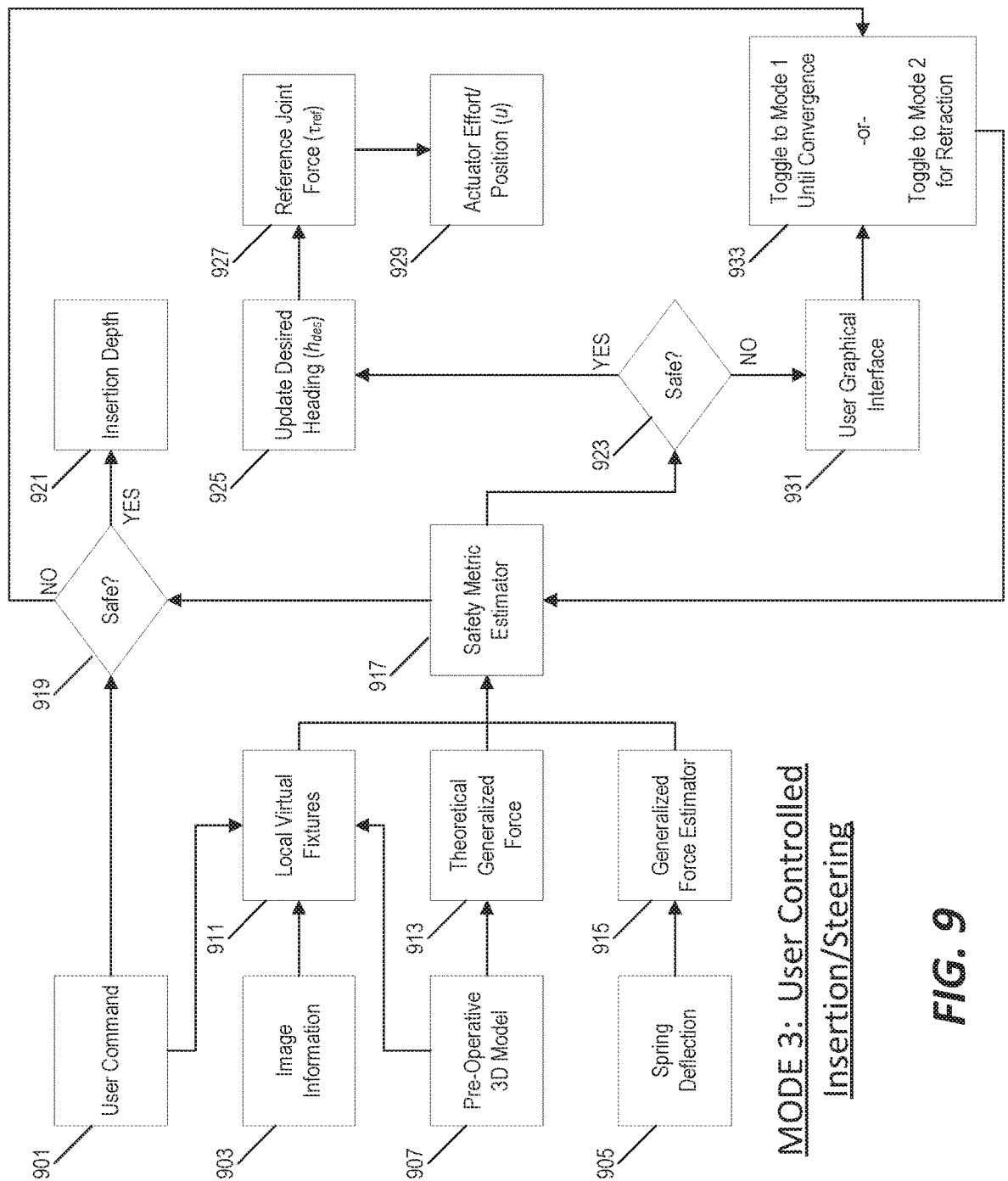
FIG. 9 is a flowchart of a method for controlling articulation of the catheter in a third mode of operation (i.e., Mode 3: User Controlled Insertion & Steering).

FIG. 8 illustrates an example of a method for implementing operation of the actuator system under Mode 2—Active Compliance. During Mode 2 operation, the user provides input commands 801 to control the insertion 807 of the catheter while the device actively complies with the surrounding environment and controls steering of the catheter tip. Accordingly, Mode 2 operation may be used, for example, during user-commanded insertion and feeding of the catheter in non-bifurcated segments of the vasculature. In this mode, the reference force $\tau_{ref}$ 815 is changed as a function of a desired heading $h_{des}$ 813 (i.e., a desired tip orientation) that will be determined based on an estimated generalized force 811 and a theoretical generalized force 809 determined based on a static model of the catheter. The estimated generalized force 811 is determined based on image information 803 from the fluoroscopic imaging system and spring deflection measurements 805.

FIG. 9 illustrates an example of a method for implementing operation of the actuator system under Mode 3—User Controlled Insertion/Steering. In some implementations, Mode 3 operation is initiated in response to a user override command. The user can choose to use a user control input (e.g., joystick 321) to drive the robot while observing the standard bi-plane fluoroscopy display (e.g., image data shown in the display of the imaging system 307 in FIG. 3A). In this mode, several background processes will run to ensure safety of the operation. A local virtual fixture law will be used to filter user commands and to determine a commanded increment of insertion depth change & an increment of change in catheter tip heading. A safety metric based on a calibrated model of the catheter and based on measurements is used to trigger a mode switch in the event of an unsafe condition being detected due, for example, to erroneous commands and/or misregistration. In some implementations, in response to detecting an unsafe condition, the system will display a notice to the user (e.g., on the display screen of the imaging system 307 of FIG. 3A) and prompt the user to elect to toggle to either Mode 1 or Mode 2. In other implementations, the system will automatically toggle to Mode 1 until convergence and then the system will revert back to Mode 3 operation. However, if after repeated toggles to Mode 1, an unsafe condition is detected, the user will be advised to toggle into Mode 2 to allow safe retraction of the catheter.

As shown in FIG. 9, the inputs used to control operation of the catheter during Mode 3 operation include user command inputs 901, image information 903 (e.g., from the fluoroscopic imaging system), measured spring deflection 905, and a pre-operative 3D model of the vasculature 907. The controller 401 is configured to define one or more local virtual fixtures 911 based on the user commands, image information, and the pre-operative 3D model. The virtual fixtures 911 define limits on the direction/distance which the catheter can be moved. Additionally, as in Mode 2 operation, the controller 401 will also determine a theoretical generalized force 913 based on a static model of the catheter and the pre-operative 3D model 907 of the vasculature. An estimated generalized force 915 is also determined based at least on the spring deflection measurements 905.

Based on the defined local virtual fixtures 911, the theoretical generalized force 913, and the estimated generalized force 915, the controller 401 then calculates an estimated safety metric 917. If the safety metric 917 indicates that further insertion or retraction of the catheter is safe (step 919), the controller 401 transmits a control signal to the linear stage actuator causing it to adjust the linear insertion depth 921. Similarly, if the safety metric 917 indicates that the bending movement corresponding to the user input command 901 is safe (step 923), the controller 401 updates the desired heading $h_{des}$ 925 and calculates a new reference joint force $\tau_{ref}$ which are, in turn, used to determine an updated motor control signal u 929 that is transmitted by the controller 401 to the actuator to cause it to adjust the bending position of the catheter. However, if the safety metric 917 indicates that the insertion command and/or the bending command based on the user input command 901 is unsafe, the system displays a notice 931 to the user on the graphical interface (e.g., the screen of the imaging system 307 in FIG. 3A) and then toggles into either Mode 1 or Mode 2 operation (step 933) (either automatically or in response to a user selection).

As discussed above, in some implementations, a 3D rendering of the vasculature and the catheter is shown on the display screen during Mode 3 operation along with a digital overlay of the location of a clot. However, user-controlled operation can be complicated in this situation because the user is interpreting the 3D images and mapping their perception of corrective action needed for steering the catheter to a proper joystick motion command. This can be simplified in Mode 3 operation by selectively filtering of "erroneous" joystick commands. For example, the controller 401 may be configured to appropriately filter an incremental heading change $\dot{h}_{des}$ (i.e., a time derivative of $h_{des}$) to help the user command the motion of the catheter only within a defined plane Π (where the plane Π is defined by the current catheter tip heading $h_{cur}$ and the heading of the local vasculature $h_{vasc}$ corresponding to the curve local tangent. Movement within this plane would be expected to be the most desirable bending movement because it would produce the shortest path for closing the heading error and would also prevent the user from having to worry about watching the ensuing motion of the catheter in the two bi-plane views.

In some implementations, this is achieved by defining $P_\Pi$ as a projection matrix that projects vectors into $\Pi$. The user input virtual fixture can then be defined as:

$$\dot{h}_{des} = k_{p1} P_\Pi \dot{h}_{user} + k_{p2}(1-P_\Pi)\dot{h}_{user} \qquad (3)$$

where $k_{p1}$ and $k_{p2}$ are proportional scaling terms and $\dot{h}_{user}$ is the incremental heading change commanded by the user command 901 (e.g., the user command received through the joystick 321). The first scaling term allows the user to move the catheter tip only in the plane. The second term allows the user to move the catheter outside the plane. Accordingly, $k_{p1} > k_{p2}$ in order to render assistive behavior without locking the user into the virtual fixture plane.

In some implementations, the bi-plane fluoroscopy images displayed on the display screen (e.g., 307 in FIG. 3A) will be augmented by the controller 401 with force information to the user that will be in the form of a color bar overlay and an auditory signal with varying pitch as a function of force at the tip of the robot.

Figure 10:
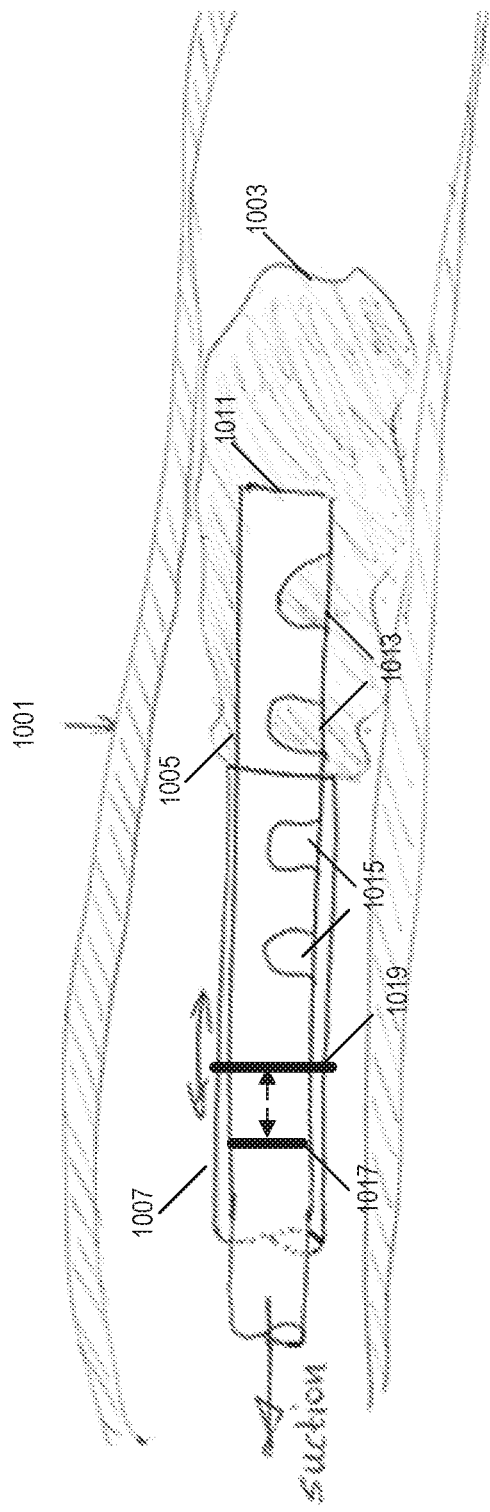
FIG. 10 is a partially transparent elevation view of a deployable catheter with side windows for increased traction when removing a clot (or thrombus).

In addition to or instead of the active and passive bending functionality described in the examples above, in some implementations, the catheter is configured with a deployable tip to provide certain functionality selectively. FIG. 10 illustrates an example of one such catheter with a deployable tip. In this example, the catheter tip is designed for retrieval of clots using a mechanism for suction. FIG. 10 shows the distal end of the catheter positioned within a blood vessel 1001 near a clot 1003. The catheter includes a central tube 1005 and a retractable outer sleeve 1007. The central tube 1005 includes an open distal end 1011 and a plurality of side windows 1013, 1015 formed in a side wall of the central tube 1005. The outer sleeve 1007 is selectively retractable to selectively expose and/or cover a desired number of side windows. For example, as shown in FIG. 10, the outer sleeve 1007 has been retracted enough to expose two of the side windows 1013 while still covering two other side windows 1015.

As described above, a suction force applied to the proximal end of the central tube 1005 causes the clot 1003 to be drawn towards the open distal end 1011 of the central tube 1005. The clot material is similarly drawn towards the exposed side windows 1013 by the applied suction force. Accordingly, the exposed side windows 1013 provide additional traction for removing the clot 1003. Furthermore, because the retractable sleeve 1007 in this example can be controlled to selectively expose only a defined number of possible side windows, the traction force applied to the clot 1003 by the catheter can be selectively tuned by adjusting the linear position of the retractable outer sleeve 1007 relative to the central tube 1005.

Additionally, in some implementations, the outer sleeve 1007 and the central tube 1005 are each equipped with a radio-opaque ring 1017 and 1019, respectively. These rings 1017, 1019 are visible in the image data captured by the fluoroscopic imaging system and can be used as a feedback control for selectively exposing only the desired number of side windows. In particular, the retracted position of the outer sleeve 1007 relative to the central tube 1005 can be determined based on a distance between the radio-opaque rings 1017, 1019 in the captured image data. Based on the known dimensions of the central tube 1005 and the outer sleeve 1007 as well as the known position of the rings 1017, 1019 thereon, the controller 401 can determine how many side windows are currently exposed and what further adjustment to the relative linear position of the outer sleeve 1007 might be necessary to expose the desired number of side windows.

Also, although the example of FIG. 10 shows a mechanism for selectively exposing side windows by retracting the outer sleeve 1007, other mechanism for exposing the side windows may be used in other implementations. For example, the catheter may be configured to selectively expose the side windows by rotation of the outer sleeve 1007 relative to the central tube 1005 instead of by linear retraction. In some such implementations, the outer sleeve 1007 will include different sections positioned around the rotational axis of the outer sleeve configured to cover some, all, or none of the side windows of the central tube 1005. Accordingly, the number of exposed side windows can be controlled by adjusting the rotational position of the outer sleeve 1007 relative to the central tube 1005 to align with one of the different sections.

Figure 11:
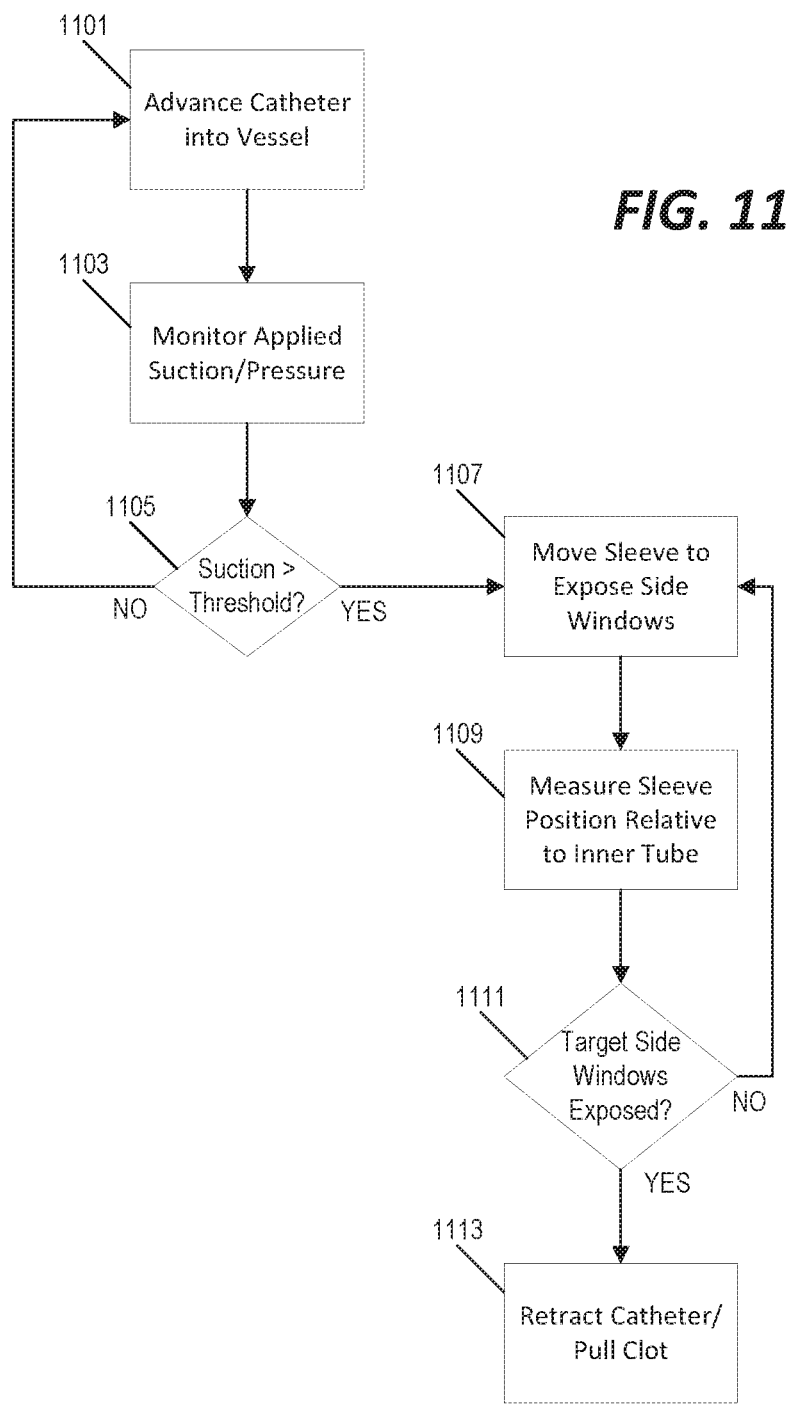
FIG. 11 is a flowchart of a method for operating the catheter of FIG. 10.

FIG. 11 illustrates one example of a method for operating the catheter of FIG. 10 to remove a clot. The catheter is advanced into the blood vessel (step 1101) while suction is applied to the proximal end of the central tube 1005. When the distal tip 1011 of the catheter contacts the clot 1003, the open distal tip 1011 will be covered/blocked by the clot 1003 and the pressure/suction applied to the central tube 1005 will increase. Therefore, the controller 401 monitors the applied pressure and suction (step 1103) and continues to advance the catheter into the blood vessel until the measured suction/pressure exceeds a defined threshold (step 1105).

Once the distal tip 1101 of the catheter has made contact with the clot, outer sleeve 1007 is moved relative to the central tube 1005 to expose the side windows (step 1107). The controller 401 continues to monitor the position of the outer sleeve 1007 relative to the central tube 1007 (step 1109) to determine when a target number of side windows have been exposed (step 1111). Once the controller 401 has determined that the desired number of side windows have been exposed, the catheter (i.e., both the outer sleeve 1007 and the central tube 1005) is retracted to pull the clot from the blood vessel (step 1113). In some implementations, the catheter is retracted automatically when a defined number of side windows have been exposed. In other implementations, a medical professional (e.g., a surgeon) makes the decision on when to initiate retraction of the catheter.

In some implementations (e.g. to assist the surgeon in determining when to initiate retraction of the catheter), the system is configured to provide an indication (e.g., a visual notice on a display screen) identifying a number of side windows that have been exposed and, in some such implementations, an indication of whether all of the exposed side windows are engaged with the clot material (as discussed in further detail below). For example, in some implementations, the system is configured to monitor the internal pressure of the central tube 1005 as the outer sleeve 1007 is retracted. When a side window is exposed and engages clot material, a relatively constant level of vacuum is maintained within the central tube 1005. However, when side windows are exposed that no longer contact the clot material, the vacuum levels within the central tube 1005 will drop. In some implementations, the system may be configured to monitor for this type of drop in pressure either while retracting the outer sleeve 1007 (e.g., to automatically stop retraction of the outer sleeve 1007 or to indicate to the operator that the additional exposed side windows are no longer contacting the clot material) and/or while retracting the catheter to pull the clot material (e.g., to determine whether traction force between the catheter and the clot material is decreasing or becoming unstable while the clot is being withdrawn).

Although the example above described "retracting" the outer sleeve 1007 to expose the side windows, in some implementations, the outer sleeve 1007 is retracted relative to the central tube 1005 by extending the central tube 1005 further into the clot 1003 while the outer sleeve 1007 remains stationary. In some implementations, extending the central tube 1005 further into the clot 1003 also helps ensure that clot material is located at the side windows when they are exposed.

Furthermore, the example of FIG. 11 shows monitoring a suction/pressure to determine when the distal tip of the central tube 1005 has come into contact with the clot. However, in some implementations, additional thresholding is used to determine when the side windows have been exposed (i.e., the suction/pressure will drop (at least temporarily) when a side window transitions from covered to exposed) and the controller 401 may be configured to use this thresholding mechanism instead of or in addition to the radio-opaque rings in order to determine when a desired number of side windows have been exposed. Also, in some implementations, additional thresholding is used after the side windows are exposed to determine when clot material has been drawn into the side windows (i.e., the suction/pressure will increase again when the side windows are obstructed by clot material) and the controller 401 may be configured to use this thresholding mechanism to initiate the retraction of the catheter only after the side windows establish additional traction with the clot material.

Finally, in some implementations, actuation of the side window mechanism may be triggered instead based on detected blood flow. In one such implementation, the system is configured to advance the catheter until a visible blood stream is detected at the proximal end of the catheter—indicating that the catheter has poked through the clot. The system then retracts the catheter until the blood stream stops—thereby indicating that the catheter tip has been fully engaged with the clot. The central tube 1005 is then axially locked in place and the outer sleeve 1007 is retracted until the blood stream is again detected. The outer sleeve 1007 is then advanced axially until the blood stream stops—indicating that the distal end of the sheath has engaged the proximal end of the clot. At this point the maximal number of side windows will be engaged with the clot for the purpose of increasing traction and the catheter is retracted to pull the clot from the blood vessel.

Figure 12A:
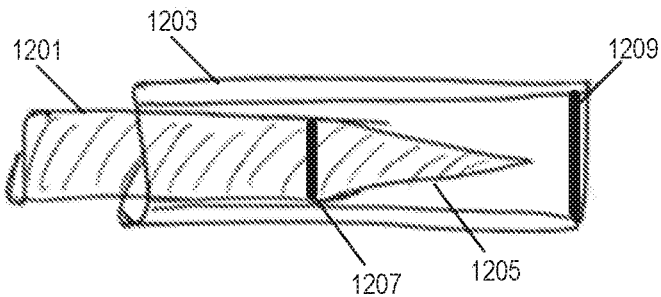
FIGS. 12A and 12B are partially transparent elevation views of a catheter with a selectively deployable, steerable tip in accordance with one embodiment shown with the steerable tip before and after deployment.
Figure 12B:
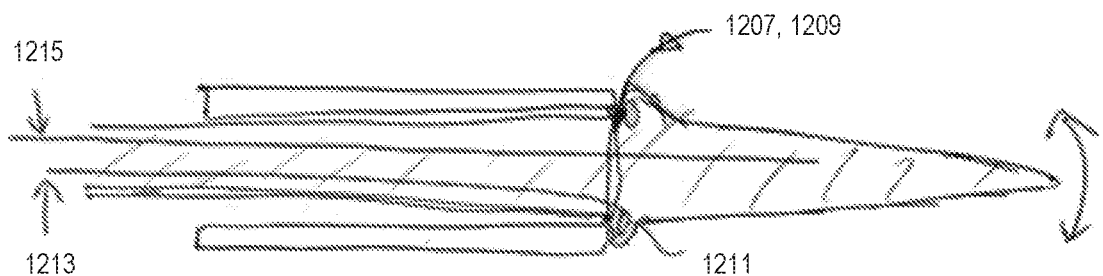

FIGS. 12A and 12B illustrates an example of another catheter device with a selectively deployable tip. In this example, an elastomeric steerable tip is selectively deployed through the distal end of the catheter. FIG. 12A shows an example of a hydraulically-operated deployable tip 1201 is positioned within a catheter tube 1203. The deployable tip 1201 includes a steerable tip 1205 Which, in the example of FIG. 12A, has not been extended beyond the distal end of the catheter tube 1203. Radio-opaque rings 1207, 1209 are coupled to the deployable tip 1201 and the catheter tube 1203 so that the position of the steerable tip 1205 can be determined relative to the catheter tube 1203 based on image data captured, for example, by the fluoroscopic imaging system (e.g, 307 in FIG. 3A).

FIG. 12B shows the steerable tip 1205 in its deployed position. In the example of FIGS. 12A and 12B, the deployable tip 1201 is operated to extend the steerable tip 1205 beyond the distal end of the catheter tube 1203 by applying hydraulic pressure to further inflate the deployable tip 1201.

As shown in FIG. 12B, the steerable tip 1205 extending beyond the distal end of the catheter tube 1202 is inflated to have a diameter that is larger than that of the catheter tube 1202 forming a pouch 1211 around the circumference of the steerable tip 1205 just beyond the distal end of the catheter tube 1202. This pouch 1211, when inflated, hold the steerable tip 1205 in its deployed position.

As discussed above in reference to FIG. 12A, one or more radio-opaque rings or markers may be positioned on the deployable tip 1201 and/or the catheter tube 1203 to provide a visual confirmation (e.g., via captured x-ray image data) that the steerable tip 1205 has been properly moved into its deployed position. In the example of FIG. 12A, there is a measurable distance between the radio-opaque rings 1207, 1209 when the steerable tip 1205 is retracted. However, in the example of FIG. 12B, the radio-opaque rings 1207, 1209 are coaxially aligned when the steerable tip 1205 is deployed.

A steering mechanism is integrated into the steerable tip 1205 to provide a controllable deflection or bending of the steerable tip 1205 when deployed. In the example of FIG. 12B, the steering mechanism includes an encapsulated bimorph actuator 1215 (e.g., a gold/polypyrole bimorph actuator) that extends into the steerable tip 1205 and controllably deflects from its central axis when a voltage is applied. This controlled deflection of the actuator 1215 pushes the steerable tip 1205 to the side from the inside, which causes the steerable tip 1205 to act as an active guide-wire. Other types of steering mechanism can be used to bend or deflect the steerable tip 1205 in other implementations. For example, the deployable tip mechanism 1201 may include a set of internal bellows that are pneumatically operated to bend the deployed tip 1205 in a desired direction by adjusting the relative inflation of the different bellows (for two DoF operation). Alternatively, the steering mechanism in some implementations may include one or more strands extending from the proximal end of the catheter each with its distal end embedded in the elastomeric material on a different internal side location of the steerable tip 1205. Deflection of the steerable tip 1205 is achieved by pushing or pulling the strands from the proximal end of the catheter.

In some implementations, a mechanical mechanism may also be provided to extend/retract the steerable tip 1205 and/or to latch the steerable tip 1205 into its deployed position. For example, FIG. 12B shows a control wire 1213 extending from the proximal end of the catheter tube 1203 to the pouch 1211 of the deployed steerable tip 1205. In some implementations, the distal end of the control wire 1213 is embedded into the elastomeric material of the steerable tip 1205 so that, when the proximal end of the control wire 1213 is pushed linearly towards the distal end of the catheter tube 1203, the steerable tip 1205 is pushed beyond the distal end of the catheter tube 1203 into its deployed position. Furthermore, to retract the steerable tip 1205 back into the catheter tube 1203, the control wire 1213 is pulled linearly towards the proximal end of the catheter tube 1203, which, in turn, pulls the steerable tip 1205 back into the interior of the catheter tube 1203. Alternatively, in some implementations, the steerable tip 1205 can be retracted by applying a pulling force to a proximal end of the elastomeric material of the deployable tip 1201.

Figure 13:
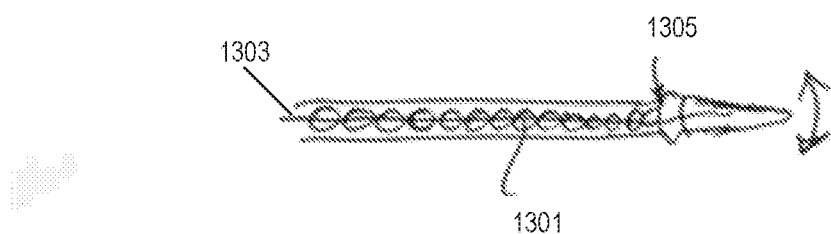
FIG. 13 is a partially transparent elevation view of a second example of a catheter with a selectively deployable, steerable tip in accordance with another embodiment.

FIG. 13 illustrates an example of another mechanism for extending the steerable tip into its deployed position. A set of serially stacked hollow beads 1301 is arranged within an elastomeric mold and are coupled to the steerable tip 1305. To deploy the steerable tip 1305, the hollow beads 1301 are pushed from the proximal end of the catheter tube toward the distal end. This pushing force transferred through the series of hollow beads 1301 pushes the steerable tip beyond the distal end of the catheter tube (as shown in FIG. 13). However, because the hollow beads are not fixedly coupled to each other in the linear direction, the catheter tube is still able to bend (passively or, in some implementations, actively) along its length.

FIG. 13 also shows a steering mechanism 1303 extending from the proximal end of the catheter tube to the steerable tip 1305. This steering mechanism can be extended through the hollow openings of the beads 1301 and operate similar to the options discussed above in reference to FIG. 12B. Also, in some implementations, the steerable tip 1305 may be locked in its deployed position by hydraulic or pneumatic inflation and/or with a control-wire-based mechanism for latching a pouch of the deployed steerable tip to the outer edge of the distal end of the catheter tube such as discussed above in reference to FIG. 12B. Finally, in some implementations, the steerable tip 1305 and the series of hollow beads 1301 can be retracted from the deployed position by applying a pulling force from the proximal end of the catheter to a control wire (e.g., control wire 1211 in FIG. 12B) or to the proximal end of the elastomeric material of the deployable tip.

Thus, in various different implementations, the invention provides, among other things, systems and methods for passive and active bending of a catheter and selectively deployable catheter tips. Other features and advantages of the invention are set forth in the accompanying claims.

What is claimed is:

1. A robotic catheter system comprising:
   an actuator including
      an active linear movement stage,
      a motor coupled to the active linear movement stage, wherein the motor is configured to control linear movement of the active linear movement stage in response to a control signal, and
      a spring coupling the active linear movement stage to a control backbone of a robotic catheter such that the linear movement of the linear movement stage causes a linear movement of the control backbone, wherein the linear movement of the control backbone causes a controllable bending of the robotic catheter;
   a sensor configured to monitor a spring deflection of the spring between the control backbone and the active linear movement stage, and to output a spring deflection signal indicative of the spring deflection detected by the sensor; and
   an electronic controller configured to
      receive the spring deflection signal from the sensor, and
      generate the control signal to the motor to control the bending of the catheter based at least in part on the spring deflection signal from the sensor.

2. The robotic catheter system of claim 1, wherein the actuator further includes a free-floating linear movement stage, wherein a proximal end of the control backbone is fixedly coupled to the free-floating linear movement stage, wherein the spring couples the active linear movement stage to the control backbone by coupling the active linear movement stage to the free-floating linear movement stage.

3. The robotic catheter system of claim 2, wherein the sensor includes a potentiometer coupled between the active linear movement stage and the free-floating movement stage, and wherein the potentiometer is configured to output the spring deflection signal based on a distance between the active linear movement stage and the free-floating movement stage.

4. The robotic catheter system of claim 1, wherein deflection of the spring allows a bending movement of the robotic catheter due to an external force applied to the robotic catheter without movement of the active linear movement stage.

5. The robotic catheter system of claim 1, wherein deflection of the spring allows an external force applied to the robotic catheter to limit a bending movement of the robotic catheter caused by movement of the active linear movement stage.

6. The robotic catheter system of claim 1, wherein a passive bending of the robotic catheter caused by an external force applied to the robotic catheter while a linear position of the control backbone remains stationary causes a second corresponding bending of the robotic catheter at another location along the length of the robotic catheter,
   wherein the electronic controller is further configured to monitor the spring deflection signal to determine the passive bending of the robotic catheter, and
   wherein the electronic controller is configured to generate the control signal by generating a control signal configured to adjust the linear position of the control backbone to prevent the second corresponding bending of the robotic catheter.

7. The robotic catheter system of claim 1, wherein the electronic controller is further configured to receive image data from an imaging system, and determine a desired heading for the catheter based on the image data, and
   wherein the electronic controller is configured to generate the control signal by generating a control signal configured to apply an active bending force to the robotic catheter by adjusting a linear position of the control backbone, wherein the active bending force is determined by the electronic controller to alter a bending of the robotic catheter from a current heading to the desired heading.

8. The robotic catheter system of claim 7, further comprising:
   a user input control; and
   a linear advancement stage configured to adjust a linear position of the robotic catheter based on a linear advancement control signal,
   wherein the electronic controller is further configured to receive a user control signal from the user input control, transmit the linear advancement control signal to the linear advancement stage to adjust the linear position of the robotic catheter based on the user control signal, and
   control a steering of the robotic catheter based on the image data and not based on the user control signal.

9. The robotic catheter system of claim 1, further comprising a user input control, wherein the electronic controller is further configured to
   receive a user control signal from the user input control,
   determine a desired heading of the robotic catheter based on the user control signal,
   receive image data from an imaging system, wherein the image data indicates dimensions of an interior cavity and a position of a distal tip of the robotic catheter in the interior cavity, and
   determine, based at leak in part on the image data, whether the desired heading violates a safety metric for operation of the robotic catheter, wherein the electronic controller is configured to generate the control signal by generating a control signal configured to apply an active bending force to the robotic catheter based on the desired heading in response to determining that the desired heading does not violate the safety metric.

10. The robotic catheter system of claim 9, further comprising a linear advancement stage configured to adjust a linear position of the robotic catheter based on a linear advancement control signal, wherein the electronic controller is further configured to
  determine a desired insertion depth of the robotic catheter based on the user control signal,
  determine, based at least in part on the image data, whether the desired insertion depth violates the safety metric for operation of the robotic catheter, and
  transmit the linear advancement control signal to move the robotic catheter to the desired insertion depth in response to determining that the desired insertion depth does not violate the safety metric.

11. The robotic catheter system of claim 9, wherein the electronic controller is further configured to filter out user control signals that indicate a desired heading that violates the safety metric.

12. The robotic catheter system of claim 9, wherein the electronic controller is further configured to change to an alternative mode of operation in response to determining that the user control signal violates the safety metric, wherein, under the alternative mode of operation, the electronic controller is configured to automatically control a steering of the robotic catheter based on the image data and not based on the user control signal.

13. The robotic catheter system of claim 9, wherein a passive bending of the robotic catheter caused by an external force applied to the robotic catheter while a linear position of the control backbone remains stationary causes a second corresponding bending of the robotic catheter at another location along the length of the robotic catheter,
  wherein the electronic controller is further configured to change to an alternative mode of operation in response to determining that the user control signal violates the safety metric, and
  wherein, under the alternative mode of operation, the electronic controller is configured to
    monitor the spring deflection signal to determine the passive bending of the robotic catheter, and
    generate the control signal configured to adjust the linear position of the control backbone only to prevent the second corresponding bending of the robotic catheter.

14. The robotic catheter system of claim 1, wherein the electronic controller is further configured to selectively operate in a first mode, a second mode, and a third mode,
  wherein the electronic controller, when operating in the first mode, is configured to allow passive bending of the robotic catheter caused by an external force applied to the robotic catheter and to adjust the linear position of the control backbone based on the spring deflection signal only to prevent additional corresponding bending of the robotic catheter induced by the passive bending,
  wherein the electronic controller, when operating in the second mode, is configured steer the robotic catheter based on image data and not based on any user control signal from a user input control, and
  wherein the electronic controller, when operating in the third mode, is configured to steer the robotic catheter based on the user control signal received from the user input control.

15. The robotic catheter system of claim 14, wherein the electronic controller, when operating in the third mode, is further configured to:
  determine whether a desired steering indicated by the user control signal violates a safety metric, and
  transition from the third mode to either the first mode or the second mode in response to determining that the desired steering violates the safety metric.

16. The robotic catheter system of claim 15, wherein the electronic controller, when operating in the third mode, is configured to transition from the third mode to either the first mode or the second mode in response to determining that the desired steering violates the safety metric by
  display a user prompt requesting the user to select between the first mode and the second mode,
  transitioning into the first mode in response to a user input selecting the first mode, and
  transitioning into the second mode in response to the user input selecting the section mode.

17. The robotic catheter system of claim 1, further comprising the robotic catheter including
  a central tube with an open distal end and a plurality of side windows formed along the length of the central tube, and
  an outer sleeve, wherein the outer sleeve is coaxially positioned around the central tube and is movable relative to the central tube from a first position where the side windows are covered by the outer sleeve and a second position where the side windows are exposed,
  wherein the robotic catheter system selectively applies a suction at a proximal end of the central tube and wherein the applied suction causes a clot material to engage the open distal end of the central tube and the exposed side windows.

18. The robotic catheter system of claim 1, further comprising the robotic catheter including an outer tube and a selectively deployable, steerable tip,
  wherein the steerable tip is formed of an elastomeric material,
  wherein the steerable tip is linearly movable relative to the outer tube between an undeployed position and a deployed position,
  wherein the steerable tip, when in the undeployed position, is positioned entirely within the outer tube,
  wherein the steerable tip, when in the deployed position, is extended beyond a distal end of the outer tube, and
  wherein the steerable tip, when in the deployed position, includes a pouch that is inflated to a diameter the is greater than an internal diameter of the outer tube such that that linear movement of the steerable tip relative to the outer tube in the direction of the undeployed position is restricted by the inflated pouch.

* * * * *